US007829576B2

(12) United States Patent
Le Bourdonnec et al.

(10) Patent No.: US 7,829,576 B2
(45) Date of Patent: *Nov. 9, 2010

(54) BELOXEPIN AND ANALOGS FOR THE TREATMENT OF PAIN

(75) Inventors: Bertrand Le Bourdonnec, East Fallowfield, PA (US); Roland E. Dolle, King of Prussia, PA (US)

(73) Assignee: Adolor Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/750,558

(22) Filed: Mar. 30, 2010

(65) Prior Publication Data

US 2010/0173927 A1 Jul. 8, 2010

Related U.S. Application Data

(63) Continuation of application No. 12/388,982, filed on Feb. 19, 2009.

(60) Provisional application No. 61/029,916, filed on Feb. 19, 2008, provisional application No. 61/050,921, filed on May 6, 2008.

(51) Int. Cl.
*A61K 31/4353* (2006.01)
*A61P 25/00* (2006.01)

(52) U.S. Cl. .................. 514/285; 514/410; 546/62; 546/61; 548/421; 548/423

(58) Field of Classification Search .................. None
See application file for complete search history.

(56) References Cited

U.S. PATENT DOCUMENTS

| | | | | |
|---|---|---|---|---|
| 4,977,158 | A | * | 12/1990 | Wieringa ............... 514/285 |
| 6,465,458 | B1 | | 10/2002 | Wong et al. |
| 6,610,690 | B2 | | 8/2003 | Wong et al. |
| 6,642,235 | B2 | | 11/2003 | Wong et al. |
| 6,703,389 | B2 | | 3/2004 | Wong et al. |
| 6,987,107 | B2 | | 1/2006 | Wong et al. |
| 7,241,762 | B2 | | 7/2007 | Wong et al. |
| 7,276,503 | B2 | | 10/2007 | Wong et al. |
| 7,317,011 | B2 | | 1/2008 | Wong et al. |
| 7,338,953 | B2 | | 3/2008 | Wong et al. |
| 2008/0275131 | A1 | | 11/2008 | Le Bourdonnec |
| 2009/0005722 | A1 | | 1/2009 | Jennlngs-Spring |
| 2009/0233957 | A1 | | 9/2009 | Le Bourdonnec |
| 2009/0233958 | A1 | | 9/2009 | Le Bourdonnec |

FOREIGN PATENT DOCUMENTS

| | | |
|---|---|---|
| WO | WO 01/62341 A2 | 8/2001 |
| WO | WO 2006/000903 A2 | 1/2006 |
| WO | WO 2007/041258 A1 | 4/2007 |
| WO | WO 2009/105507 A2 | 8/2009 |

OTHER PUBLICATIONS

Sindrup et al. in Basic and Clinical Pharmacology & Toxicology 2005, 96, 399-409.*
van Bemmel et al. in Neuropsychobiology 1999, 40:107-114.*
Amitriptyline Injection (www.goldbamboo.com/topic-t4747. html.).*
Nagakura et al. in the Journal of Pharmacology and Experimental Therapeutics 306:490-497, 2003.*
Amitriptyline Injection (www.goldbamboo.com/topic-t4747.html.) (published online Jun. 1, 2005).*
Aragona et al., 2005, "Randomized double-blind comparison of serotonergic (Citalopram) versus noradrenergic (Reboxetine) reuptake inhibitors in outpatients with somatoform, DSM-IV-TR pain disorder," *European Journal of Pain* 9(1):33-38.
Atkinson et al., 1999, "Effects of Noradrenergic and Serotonergic Antidepressants on Chronic Low Back Pain Intensity," *Pain* 83(2):137-145.
van Bemmel et al., 1999, "The Acute Effects of the Noradrenaline Reuptake Inhibitor Org 4428 on EEG Sleep in Healthy Volunteers," *Neuropsychobiology* 40: 107-114.
Bomholt et al., 2005, "Antinociceptive Effects of the Antidepressants Amitriptyline, Duloxetine, Mirtazapine and Citalopram in Animal Models of Acute, Persistent and Neuropathic Pain," *Neuropharmacology* 48(2):252-263.
Bymaster et al., 2005, "The Dual Transporter Inhibitor Duloxetine: A Review of Its Preclinical Pharmacology, Pharmacokinetic Profile, and Clinical Results in Depression," *Current Pharmaceutical Design* 11:1475-1493.
Canavero et al., 2002, "Reboxetine for Central Pain: A Single-Blind Prospective Study," *Clinical Neuropharmacology* 25(4):238-239.
Canavero et al., 2004, "Norepinephrine and Pain," *Pain* 107(3):279.
Claghorn et al., 1996, "Recent Developments in Antidepressant Agents," *Progress in Drug Research* 46:243-262.
Collins et al., 2000, "Antidepressants and Anticonvulsants for Diabetic Neuropathy and Postherpetic Neuralgia: A Quantitative Systematic Review," *Journal of Pain an Symptom Management* 20(6):449-458.
Crowell et al., 2004, "Antidepressants in the Treatment of Irritable Bowel Syndrome and Visceral Pain Syndromes," *Current Opinion in Investigational Drugs* 5(7):736-742.
Demling, 1996, "Tetrazyklishe Antidepressiva: Pharmakologisch-klinische Aspekte unde Neuentwicklungen," *Nevernheilkunde* 15:92-100 (English language abstract).
Freynhagen et al., 2006, "Mirtazapine and its enantiomers differentially modulate acute thermal nociception in rats," *Brain Research Bulletin* 69:168-173.
Goldstein et al., 2005, "Duloxetine vs. Placebo in Patients with Painful Diabetic Neuropathy," *Pain* 116:109-118.
Hashimoto et al., 1996, "Serotonin Reuptake Inhibitors Reduce Conditioned Fear Stress Induced Freezing Behavior in Rats," *Psychopharmacology* 123:182-186.

(Continued)

*Primary Examiner*—Brandon J Fetterolf
*Assistant Examiner*—Dennis Heyer
(74) *Attorney, Agent, or Firm*—Dechert LLP

(57) ABSTRACT

This present disclosure provides methods of treating pain with beloxepin and/or beloxepin analogs.

18 Claims, 16 Drawing Sheets

OTHER PUBLICATIONS

Figure 6A:
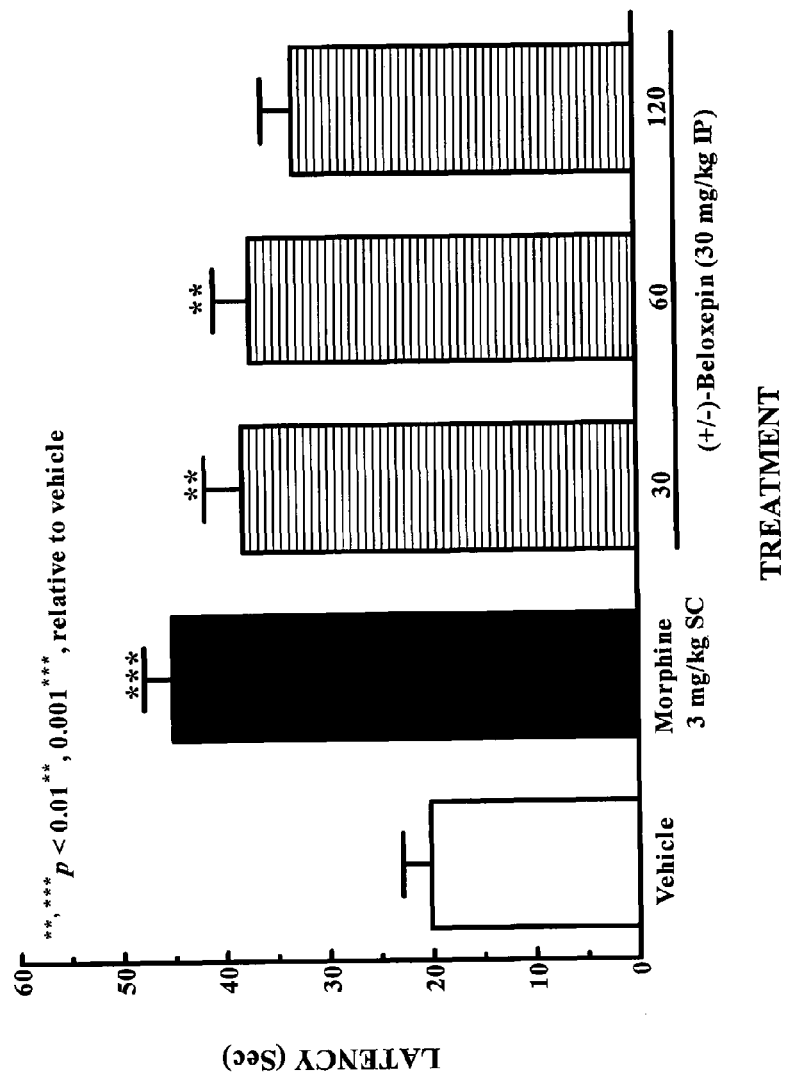

International Search Report and the Written Opinion, Notification of Transmittal of, of the International Searching Authority or the Declaration dated May 14, 2009 for Application No. PCT/US2009/34461.

Iyengar et al., 2004, "Efficacy of Duloxetine, a Potent and Balanced Serotonin-Norepinephrine Reuptake Inhibitor in Persistent Pain Models in Rats," *The Journal of Pharmacology and Experimental Therapeutics* 311(2): 576-584.

Jones et al., 2005, "Efficacy of Duloxetine, a Potent and Balanced Serotonergic and Noradrenergic Reuptake Inhibitor, in Inflammatory and Acute Pain Models in Rodents," *The Journal of Pharmacology and Experimental Therapeutics* 312(2):726-732.

Jones et al., 2006, "Analgesic effects of serotonergic, noradrenergic or dual reuptake inhibitors in the carrageenan test in rats: Evidence for synergism between serotonergic and noradrenergic reuptake inhibition," *Neuropharmacology* 51(7-8):1172-1180.

Krell et al., 2005, "Evaluation of Reboxetine, A Noradrenergic Antidepressant, for the Treatment of Fibromyalgia and Chronic Low Back Pain," *Psychosomatics* 46(5):379-384.

Leventhal et al., 2007, "Differential and Synergistic Effects of Selective Norepinephrine and Serotonin Reuptake Inhibitors in Rodent Models of Pain," *The Journal of Pharmacology and Experimental Therapeutics* 320(3):1178-1185.

Mahaney et al., 2008—published on the Web Jun. 17, 2008, "Structure-Activity Relationships of the Cycloalkanol Ethylamine Scaffold: Discovery of Selective Norepinephrine Reuptake Inhibitors," *J. Med. Chem.* 51(13): 4038-4049.

Max et al., 1992, "Effects of Desipramine, Amitriptyline, and Fluoxetine on Pain in Diabetic Neuropathy," *The New England Journal of Medicine* 326(19):1250-1256.

Muth-Selbach et al., 2009, "Racemic intrathecal mirtazapine but not its enantiomers acts anti-neuropathic after chronic constriction injury in rats," *Brain Research Bulletin* 79:63-68.

Obata et al., 2005, "Spinal noradrenaline transporter inhibition by reboxetine and Xen2174 reduces tactile hypersensitivity after surgery in rats," *Pain* 113(3):271-276.

Paanakker et al., 1998, "Validation of an LC-MS Assay for the Quantification of the Enantiomers of Org 4428 In Human Plasma," *J. Pharm. Biomed. Anal.* 16:981-989.

Pederson et al., 2005, "Anti-nociception is Selectively Enhanced by Parallel Inhibition of Multiple Subtypes of Monoamine Transporters in Rat Models of Persistent and Neuropathic Pain," *Psychopharmacology* 182(4):551-561.

Schreiber et al., 1998, "Interaction between the tetracyclic antidepressant mianserin HCl and opioid receptors," *European Neuropsychopharmacology* 8:297-302.

Schreiber et al., 2009, "The antinociceptive properties of reboxetine in acute pain," *European Neuropsychopharmacology*, 19(10): 735-739.

Sindrup et al., 1999, "Efficacy of Pharmacological Treatments of Neuropathic Pain: An Update and Effect Related to Mechanism of Drug Action," *Pain* 83:389-400.

Sperling et al., 1997, "New Tetracyclic Antidepressants," *Drugs of Today* 33(2):95-102.

Tatsumi et al., 1997, "Pharmacological profile of antidepressants and related compounds at human monoamine transporters," *European Journal of Pharmacology* 340:249-258.

Wernicke, 2007, "Treatment of Chronic Pain with Drugs that Modulate Central Nervous System Serotonin and Norepinephrine," *Current Drug Therapy* 2(2): 161-167.

Wikström et al., 2002, "Synthesis and Pharmacological Testing of 1,2,3,4,10,14b-Hexahydro-6-methoxy-2-methyldibezo[c,f,]Apyrazinol[1,2-a]azepin and Its Enantiomers in Comparison with the Two Antidepressants Mianserin and Mirtazapine," *Journal of Medicinal Chemistry* 45:3280-3285.

Yalcin et al., 2009, "$\beta$2-adrenoceptors are essential for desipramine, venlafaxine or reboxetine action in neuropathic pain," *Neurobiology of Disease* 33(3):386-394.

Zhang, 2009, "1- or 3-(3-amino-2-hydroxy-1-phenyl propyl)-1,3-dihydro-2*H*-benzimidazol-2-ones: Potent, Selective, and Orally Efficacious Norepinephrine Reuptake Inhibitors," *J. Med. Chem.* 52(18):5703-5711.

ORG-4428: CNS Testing Phase III (Internal Report), 5 pages, Feb. 19, 1999.

Pharmacological Data for ORG-2448 (Internal Report), 4 pages, Feb. 19, 1999.

Investigation's Brochure for ORG-4428 Capsules, 3 pages, Feb. 19, 1999.

\* cited by examiner

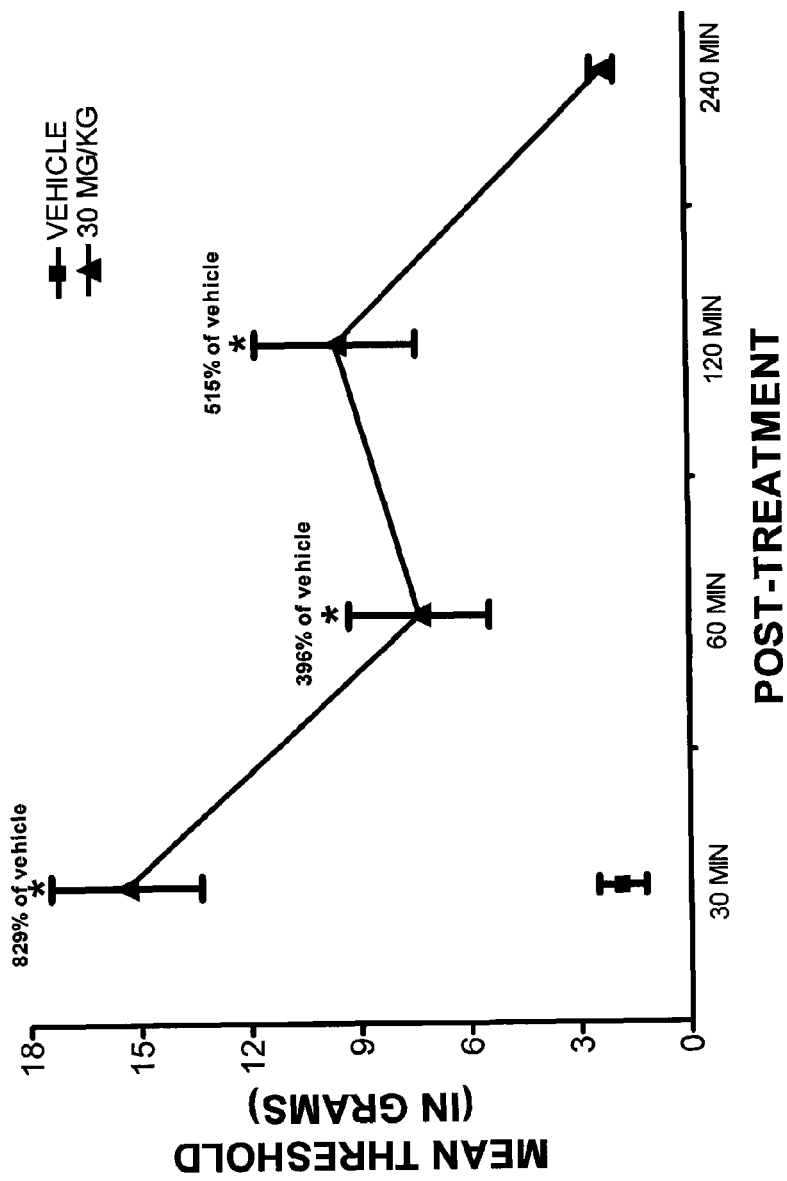

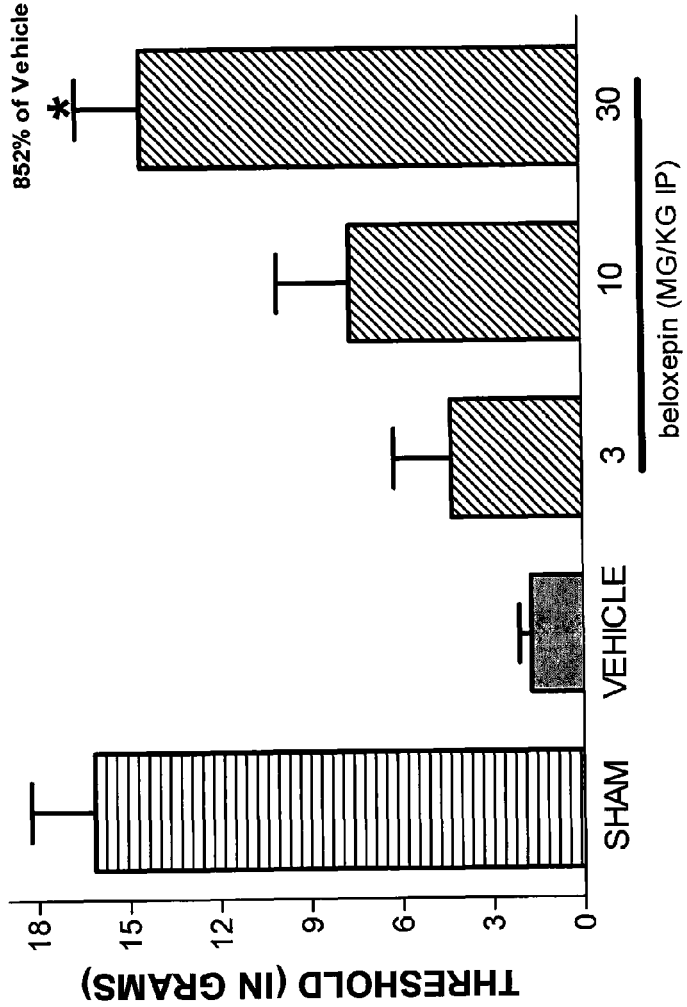

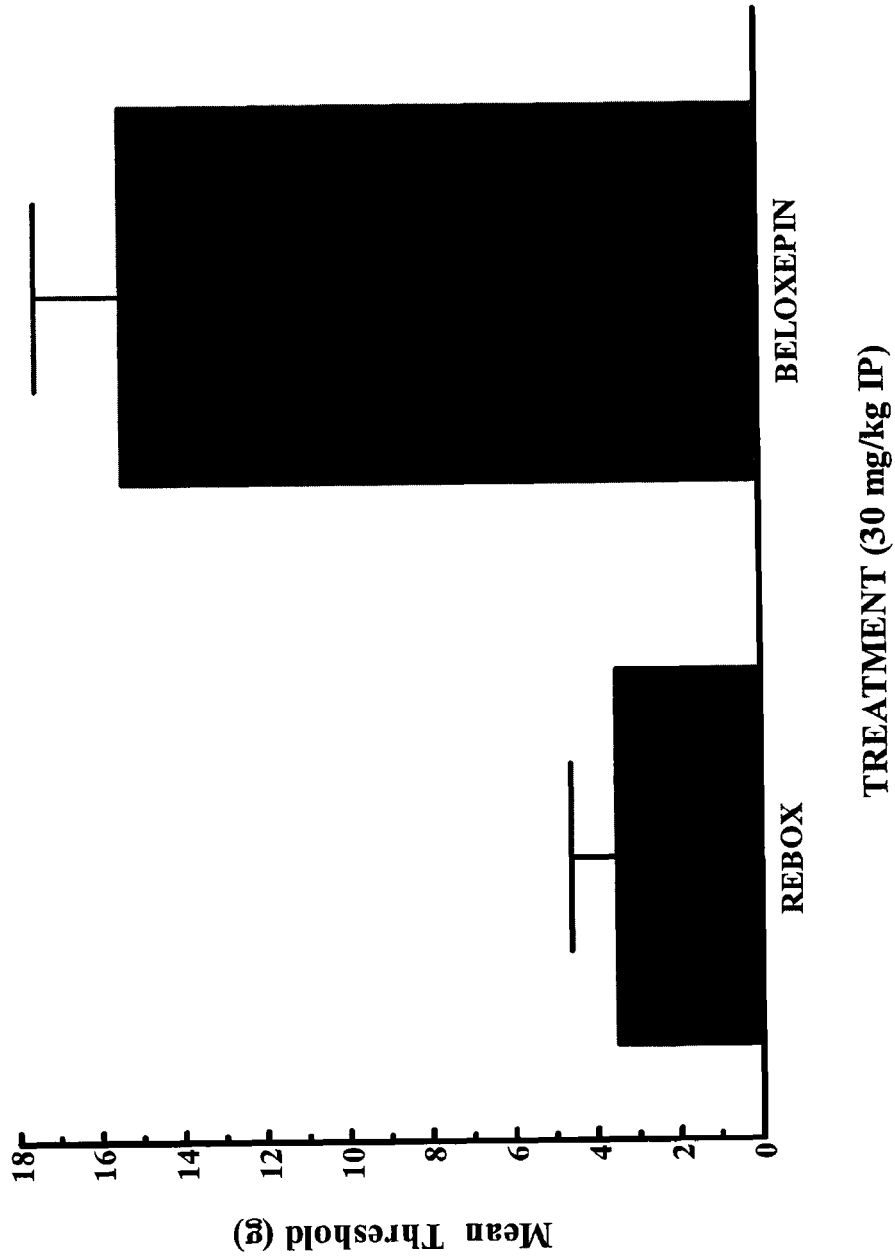

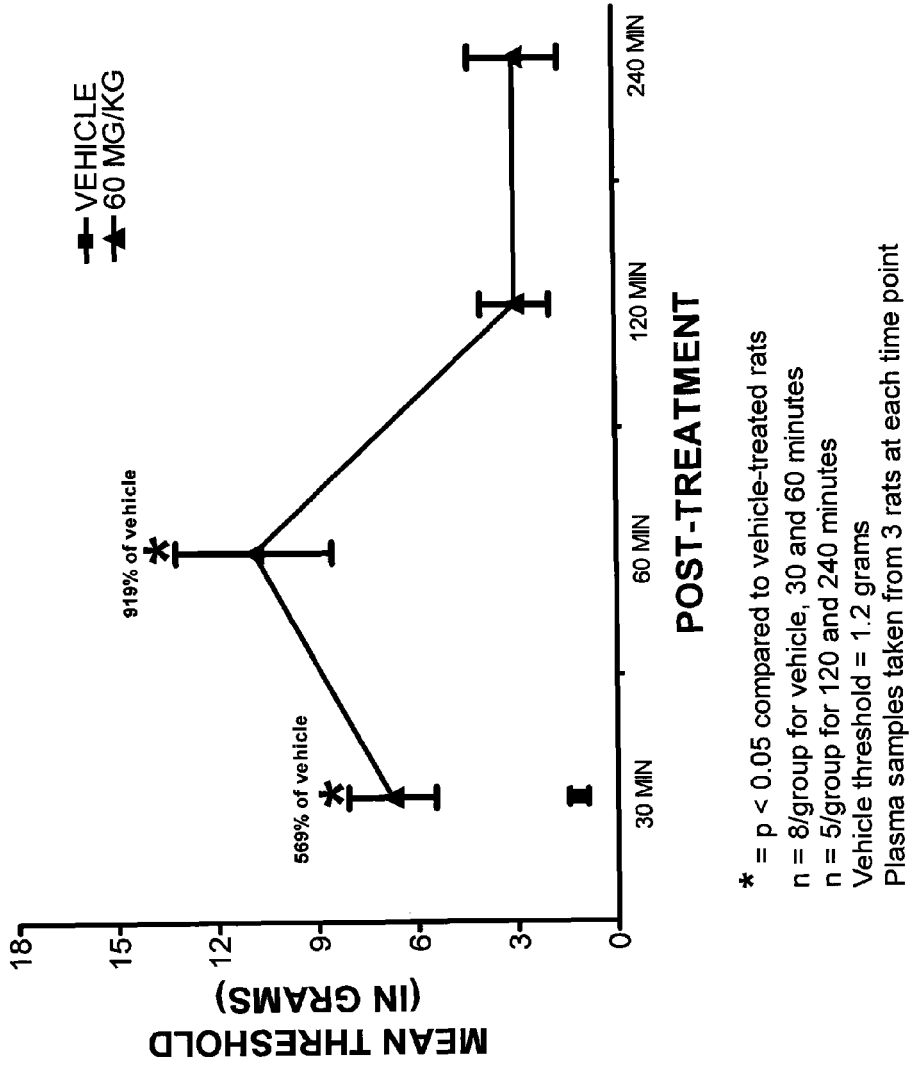

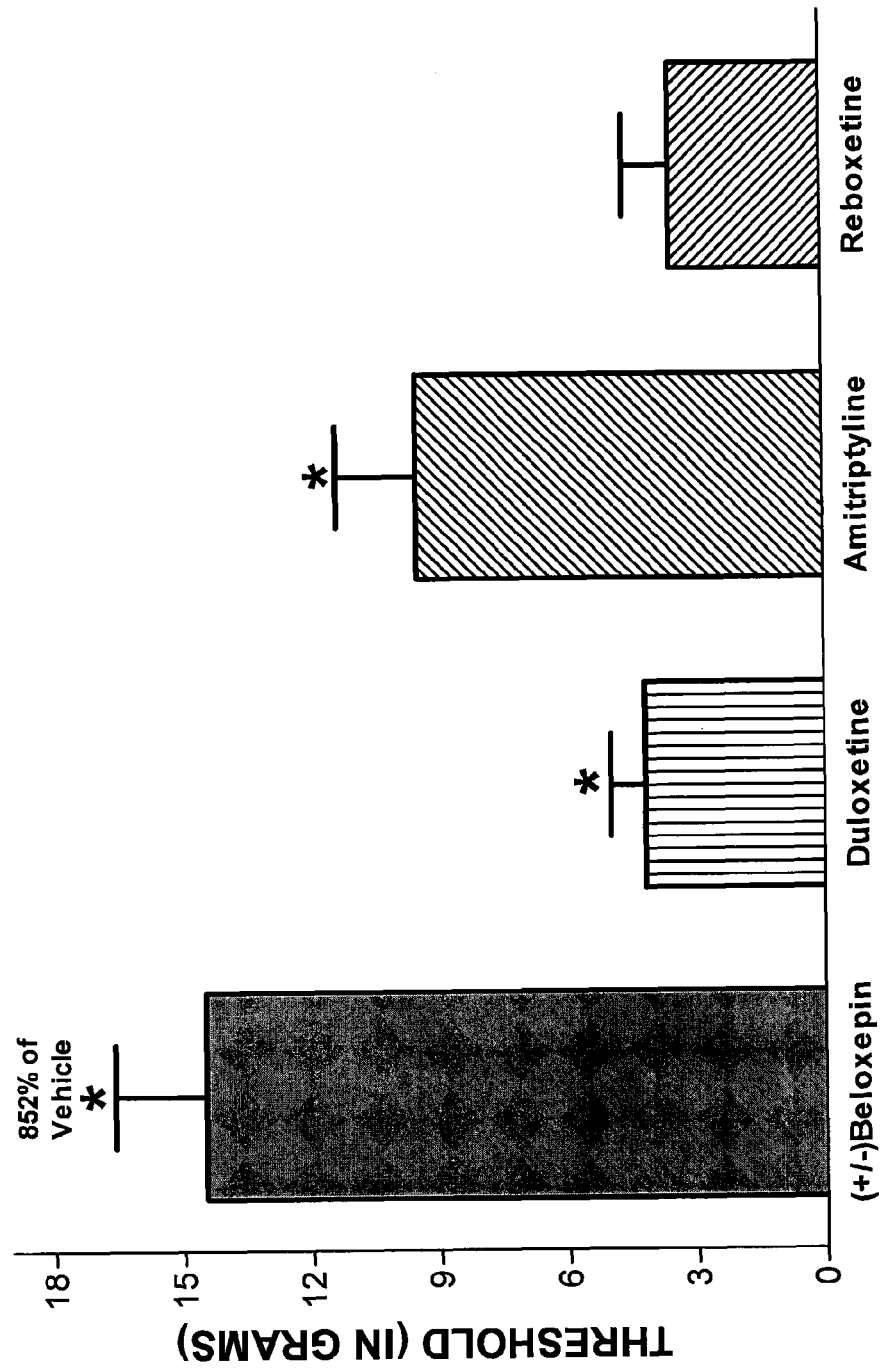

Antinociceptive Effect of (+/-)-Beloxepin in the Rat 50 °C Hot Plate (+/−)-Beloxepin Reverses FCA-Induced Mechanical Hyperalgesia in 24 h FCA-Treated Rats Inhibition of Acetic Acid-Induced Writhing by (+/−)-Beloxepin in Mice Mechanical Antihyperalgesic Effect of (±)-Beloxepin (Lot 7) and Reconstituted Racemic Mixture (Lot 9) in 24 h FCA-Treated Rats Antiallodynic Effect of Beloxepin (60 mg/Kg PO) in the Rat L5 SNL Model Antiallodynic Effect of Beloxepin, Duloxetine, and Esreboxetine (30 mg/Kg IP) in the Rat L5 SNL Model Antiallodynic Effect of Beloxepin (60 mg/Kg PO) – Hindpaw Incision Model Inhibition of CYP2D6 (dextromethorphan O-demethylation) by Beloxepin

BELOXEPIN AND ANALOGS FOR THE TREATMENT OF PAIN

1. CROSS REFERENCE TO RELATED APPLICATIONS

This application is a continuation of application Ser. No. 12/388,982, filed Feb. 19, 2009, currently pending, which claims the benefit of provisional application Ser. No. 61/029,916, filed Feb. 19, 2008, and provisional application Ser. No. 61/050,921, filed May 6, 2008, the disclosures of which are incorporated herein by reference in their entireties.

2. STATEMENT REGARDING FEDERALLY SPONSORED RESEARCH

None.

3. PARTIES TO A JOINT RESEARCH AGREEMENT

None.

4. REFERENCE TO SEQUENCE LISTING, TABLE OR COMPUTER PROGRAM

None.

5. BACKGROUND

Acute and chronic pain of both nociceptive and non-nociceptive origin are disabling conditions that affect significant numbers of individuals. Pain is frequently characterized by increased sensitivity to normally non-noxious stimuli (allodynia) and/or painful stimuli (hyperalgesia). Although antidepressants such as norepinephrine and serotonin (5HT) reuptake inhibitors have been used as a first-line therapy for treating certain types of pain, for example, pain associated with diabetic neuropathy, postherpetic neuralgia, fibromyalgia, irritable bowel syndrome and interstitial cystitis, none of these therapies has proven to be universally effective. Despite the number of therapies available, significant numbers of individuals still suffer debilitating pain on a daily basis. Accordingly, there is a need in the art for additional compounds and regimens useful for treating pain, whether acute or chronic, or due to nociceptive or non-nociceptive origin.

6. SUMMARY

Beloxepin, also known as "Org-4428" and "cis-1,2,3,4,4a,13b-hexahydro-2,10-dimethyldiben-[2,3:6,7]oxepino[4,5c]pyridine-4a-ol]," is a tetracyclic compound that underwent clinical evaluation as a potential antidepressant in the late 1990s. According to published reports, beloxepin is a highly specific inhibitor of noradrenaline reuptake in synaptosomes from rat and primate brain in in vitro assays, having greater than 100-fold less affinity for other monoamine carriers (i.e., serotonin and dopamine transporters), and no or very weak affinity for noradrenergic, histaminergic and cholinergic receptors (Sperling & Demling, 1997, Drugs of Today 33(2):95-102). It is also reported to have modest affinity for the $5HT_{2C}$ receptor (Claghorn & Lesem, 1996, Progress Drug Res 46:243-262).

In preclinical studies with animal models of depression, beloxepin was noted to exhibit antidepressant properties by offsetting acquired immobility behavior, reserpine-induced hypothermia, and conditioned avoidance behavior. In these tests, beloxepin did not cause sedation, motor impairment or other untoward side effects. Its profile on EEG-defined sleep/wake behavior is compatible with that of a nonsedative antidepressant with sleep-improving properties (Sperling & Demling, 1997, supra). Results of sleep studies in human volunteers have shown that beloxepin (25-400 mg) dose-dependently prolonged REM latency, both acutely and subchronically, and decreased total duration of nocturnal REM sleep as recorded by EEG (Van Bemmel et al., 1999, Neuropsychobiology 40(2):107-114). No sedation or other side effects were observed. Based on these studies, it was concluded that beloxepin may reduce sleep continuity in depressed patients and may improve the depth of sleep.

In a single-dose safety study, beloxepin displayed linear kinetics over a broad range, with a dose-independent $t_{max}$ of one to four hours and $t_{1/2}$ of 11 to 15 hr following doses of 10 to 500 mg. Steady-state pharmacokinetic parameters obtained in healthy normal subjects, who participated in a multiple rising-dose safety and tolerance study, showed that at doses of 50 to 800 mg, $t_{max}$ was 1.17 hr and $t_{1/2}$ varied from 12 to 14 hr. No important adverse effects were observed in healthy volunteers who received up to 800 mg/day of beloxepin. In a phase IIA study in patients hospitalized for depression, ⅔ of patients had a moderate to good response, based on HAMD score reduction (Claghorn & Lesem, 1996, supra).

In subsequent clinical trials, beloxepin exhibited insufficient efficacy for the treatment of major depression. Consequently further development of beloxepin was stopped (Paanakker et al., 1998, J. Pharm. Biomed. Anal. 16(6):981-989).

Affinity testing with over 125 receptors, channels and transporters indicates that beloxepin binds with only modest affinity to the NET ($K_i$=700 nM) and has only marginal affinity for the serotonin transporter (27% inhibition of binding at 10 µM in a competition assay) and dopamine transporter (16% inhibition of binding at 10 µM in a competition assay). In a functional assay, beloxepin exhibited weak inhibition of norepinephrine reuptake ($IC_{50}$=130 nM).

Historically, antidepressants including those that inhibit reuptake of NE (NRIs) and/or 5HT (SRIs) have been used as a first-line therapy for treating both acute and chronic pain that is either nociceptive or non-nociceptive in origin, for example, neuropathy, post-herpetic neuralgia (PHN), pain associated with fibromyalgia, pain associated with irritable bowel syndrome and interstitial cystitis (Sindrup and Jensen, 1999, Pain 83(3):389-400; Collins et al., 2000, J. Pain & Symptom Management 20(6):449-458; Crowell et al., 2004, Current Opin. Invest. Drugs 5(7):736-742). A recent study systematically evaluated the relative activity at the NE and/or 5HT transporter required for maximal efficacy in rodent models of pain (Leventhal et al., 2007, J. Pharmacol. Exper. Ther. 320(3):1178-1185). The effects observed replicate those observed clinically for treating neuropathic pain conditions. Namely, compounds with greater affinity for the NE transporter are more effective at treating pain, and compounds with greater affinity for the 5HT transporters have limited efficacy (see, e.g., Max et al., 1992; N. Engl. J. Med. 326(19):1250-1256; Collins et al., 2000, supra). Indeed, in a double-blind, placebo-controlled head-to-head study comparing the tetracyclic NRI maprotiline and the SRI paroxetine, reduction in pain intensity was significantly greater for study completers randomized to maprotiline (45%) as compared to paroxetine (26%) or placebo (27%) (Atkinson et al., 1999, Pain 83(2):137-145).

Given its weak affinity for the NET and its weak, albeit selective, inhibition of NE reuptake, beloxepin would not be expected to be effective in treating pain. Surprisingly, the present inventors have discovered that not only is beloxepin extremely effective in rodent models of various different pain syndromes, its antiallodynic activity is superior to that of known NRI compounds (e.g., reboxetine), dual NRI/SRI compounds (e.g., duloxetine) and tricyclic antidepressants (e.g., amitriptyline) currently used to treat pain when dosed at the same concentrations via IP administration.

Indeed, the magnitude of tactile allodynia observed for beloxepin in the L5 SNL rodent model of pain at 30 min post treatment is amongst the highest observed by the inventors in this model for drugs administered IP. Also see FIG. 11 and Example 10, presenting a comparison of the antiallodynic effects observed upon administration beloxepin, duloxetine, and esreboxitine using the rat L5 SNL model system.

As demonstrated in FIG. 3, beloxepin produced an observed mean threshold of approximately 15 g—nearly 5 times greater—under the same experimental conditions than reboxetine. With reference to FIG. 2, beloxepin produced a tactile antiallodynic effect that was 852% greater than that observed with vehicle-treated controls, and nearly 100% of that observed with sham-operated animals.

Figure 7:
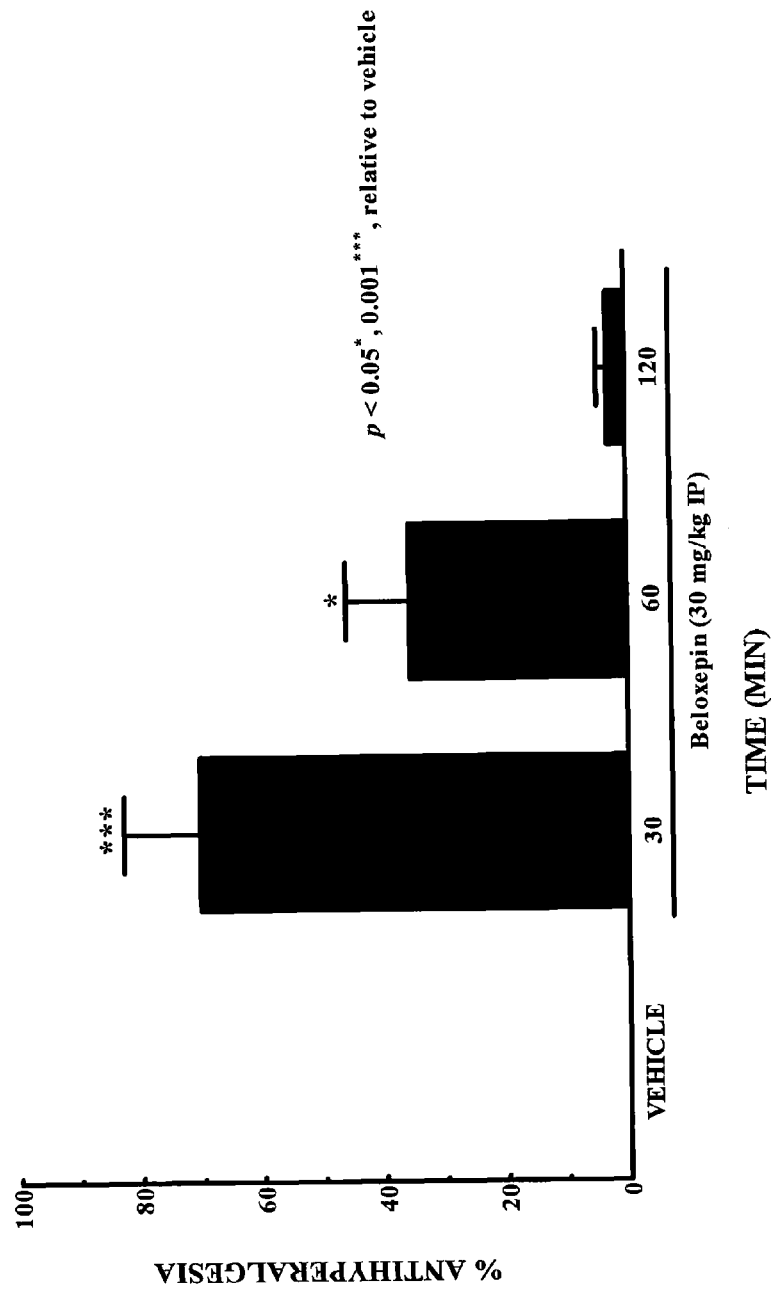
Figure 8:
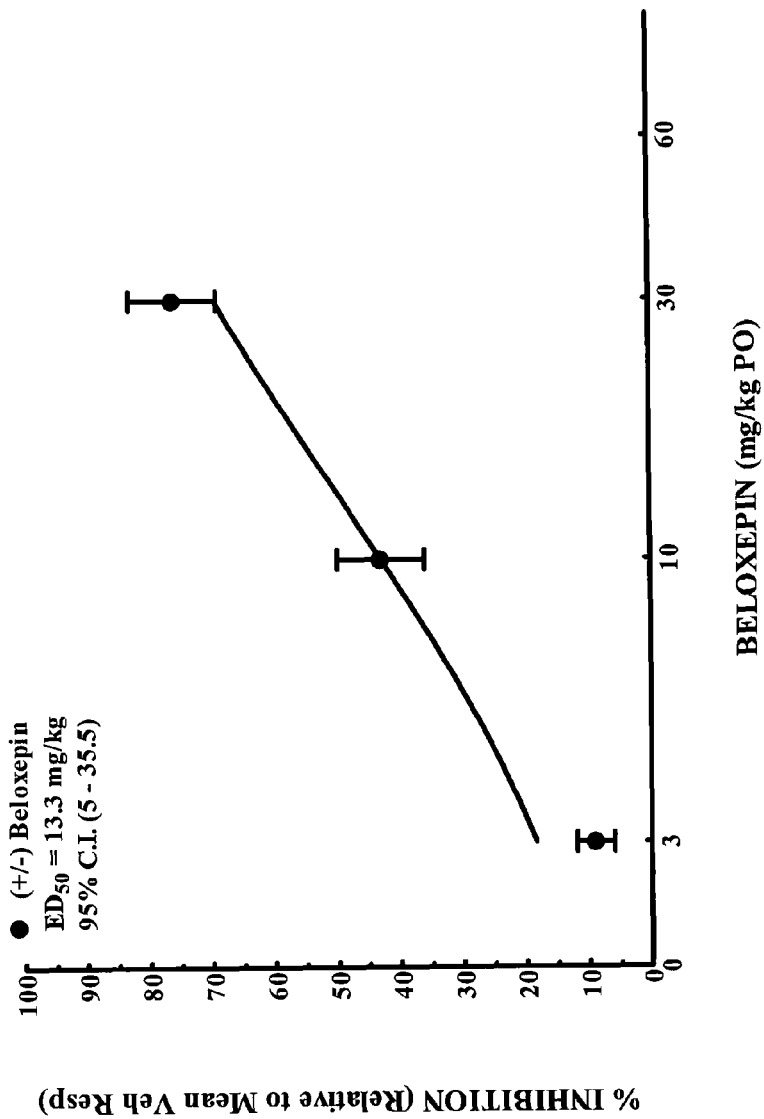

Beloxepin also exhibited extremely robust activity in rodent models of acute nociceptive pain (FIGS. 6A and 6B), inflammatory pain (FIG. 7 and FIG. 9), neuropathic pain (FIG. 10 and Example 12), post-operative incisional pain (FIG. 12, FIG. 13, FIG. 14, and Example 13), and visceral pain (FIG. 8). For example, with reference to FIGS. 6A and 6B, beloxepin exhibited anti-nociceptive activity almost equivalent to that of 3 mg/kg morphine. With reference to FIG. 7, beloxepin exhibited nearly complete reversal of hyperalgesia in rats treated with Freund's Complete Adjuvant (FCA), and with reference to FIG. 8, beloxepin inhibited acetic acid-induced writhing in mice a dose-dependent fashion.

The chemical structure of beloxepin is illustrated below:

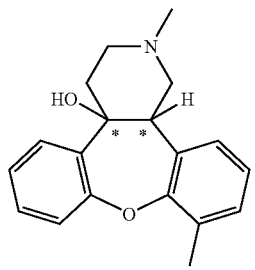

The OH and H substituents attached to the carbon atoms marked with asterisks are in the cis configuration with respect to one another. These carbon atoms are chiral. As a consequence, beloxepin is a racemic mixture of two cis enantiomers, a (+) enantiomer and a (−) enantiomer. The absolute configurations about the chiral carbons of the (+) and (−) enantiomers are unknown.

Analogs of beloxepin are known in the art. For example, analogs of beloxepin are described in U.S. Pat. No. 4,977, 158, the disclosure of which is incorporated herein by reference. These analogs are expected to exhibit anti-pain activities similar to beloxepin.

Accordingly in one aspect, the present disclosure provide a method of treating pain in a mammal comprising administering to a mammal suffering from pain, including a human, an amount of beloxepin and/or a beloxepin analog effective to treat the pain.

The beloxepin or beloxepin analog can be administered as the compound per se, or in the form of a composition. The beloxepin or beloxepin analog can be included in the composition as the free base, or in the form of a salt. In some embodiments the beloxepin and/or beloxepin analog is included in the composition in the form of a pharmaceutically acceptable salt.

The composition can be formulated for administration to animals in veterinary contexts, or for administration to humans, via virtually any route or mode of administration, including, but not limited to, oral, topical, ocular, buccal, systemic, nasal, injection, transdermal, rectal, vaginal, inhalation or insufflation. In some embodiments, the composition is formulated for oral administration, for example, to humans.

The methods can be used to treat numerous different types of pain syndromes, including acute or chronic pain that is either nociceptive (for example somatic or visceral) or non-nociceptive (for example neuropathic or sympathetic) in origin. In some embodiments, the pain is nociceptive pain including, but not limited to, surgical pain, inflammatory pain such as that associated with inflammatory bowel syndrome ("IBS") or rheumatoid arthritis, pain associated with cancer, and pain associated with osteoarthritis. In some embodiments, the pain is non-nociceptive pain including, but not limited to, neuropathic pain such as post-herpetic neuralgia ("PHN"), trigeminal neuralgia, focal peripheral nerve injury, anesthesia clolorosa, central pain (for example, post-stroke pain, pain due to spinal cord injury or pain associated with multiple sclerosis), and peripheral neuropathy (for example, diabetic neuropathy, inherited neuropathy or other acquired neuropathies).

The beloxepin and/or beloxepin analog can be administered alone, or it can be administered in combination with, or adjunctively to, one or more other drugs useful for treating pain and/or other indications. Specific non-limiting examples of drugs that can be used in combination with, or adjunctively to, the beloxepin and/or beloxepin analogs in a pain treatment or management regimen are provided in a later section. In one specific embodiment, beloxepin is administered in combination with, or adjunctively to, one or more beloxepin analogs.

7. BRIEF DESCRIPTION OF THE FIGURES

Figure 6B:
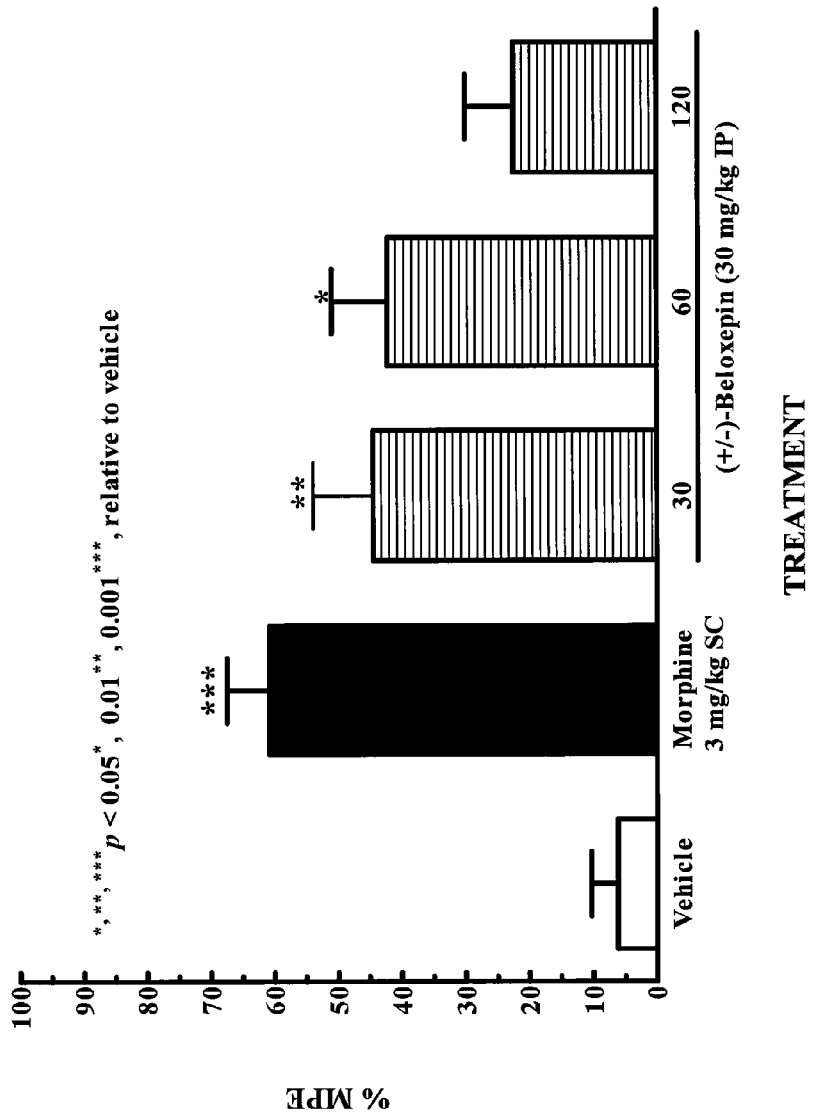
Figure 9:
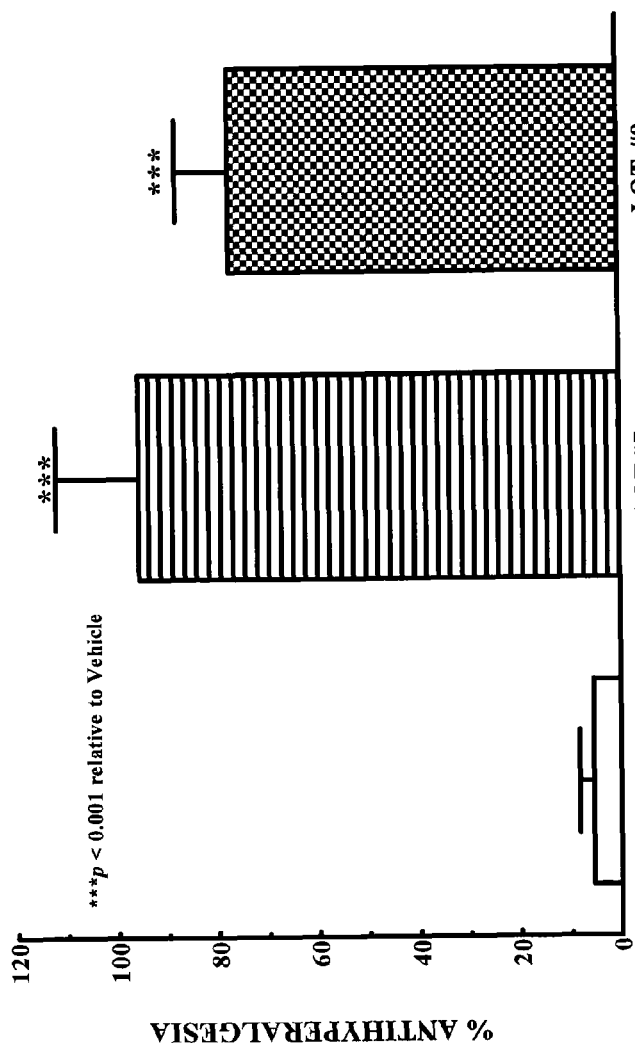
Figure 10:
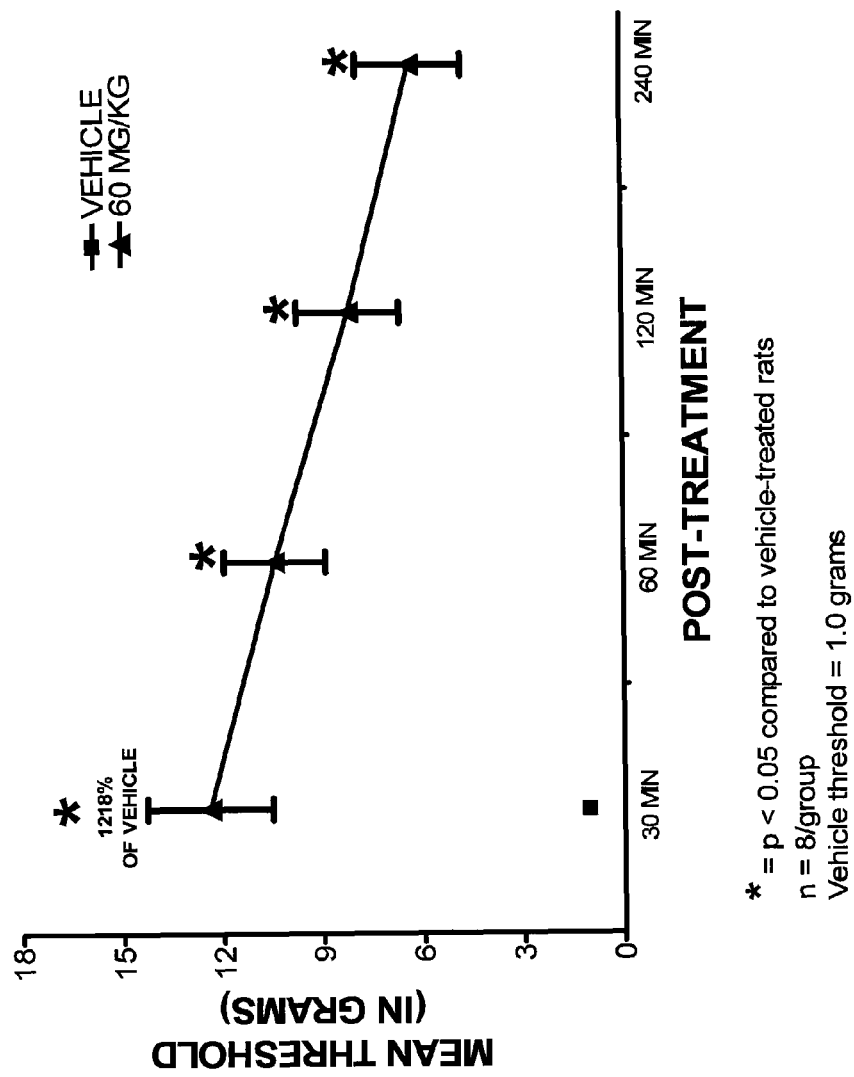
Figure 11:
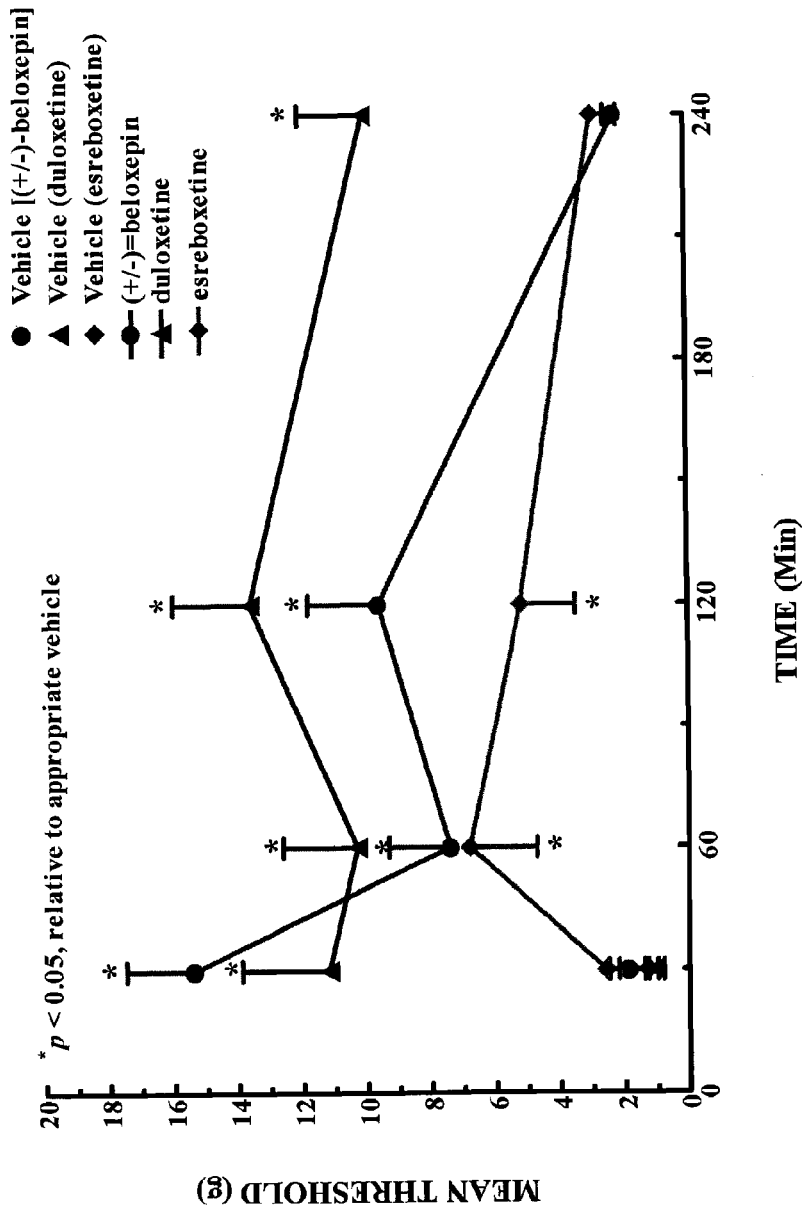
Figure 12:
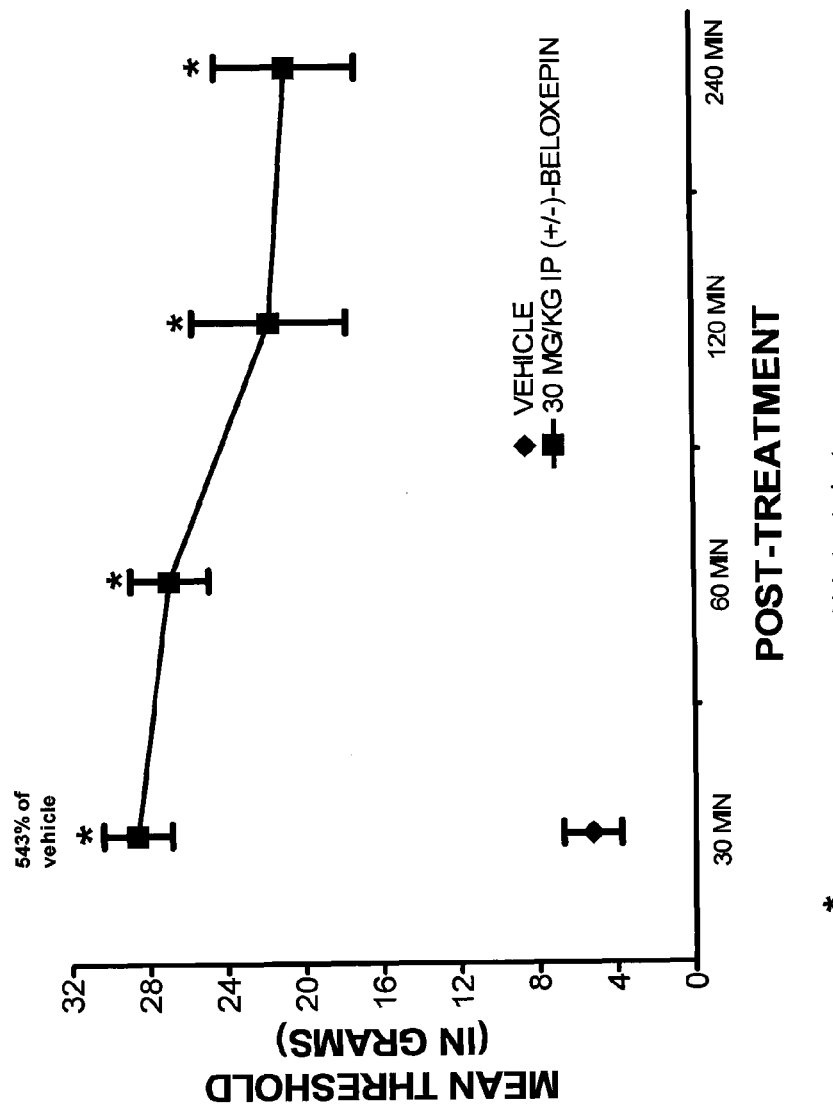
Figure 13:
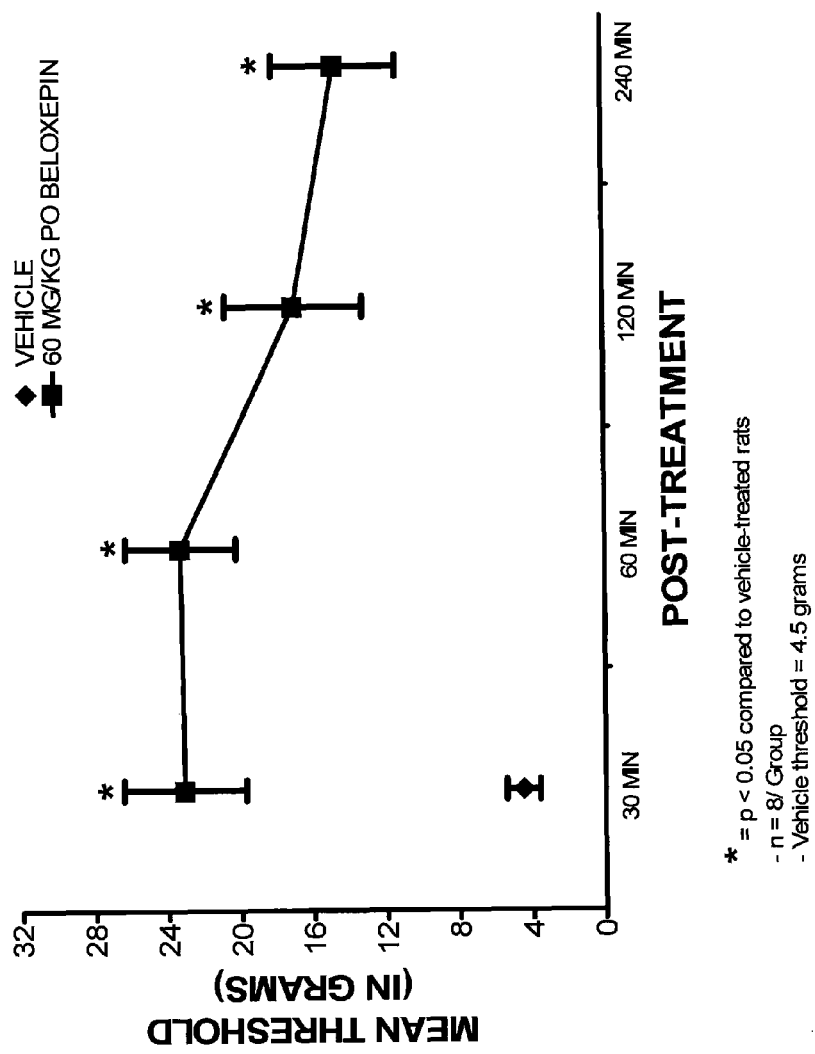
Figure 14:
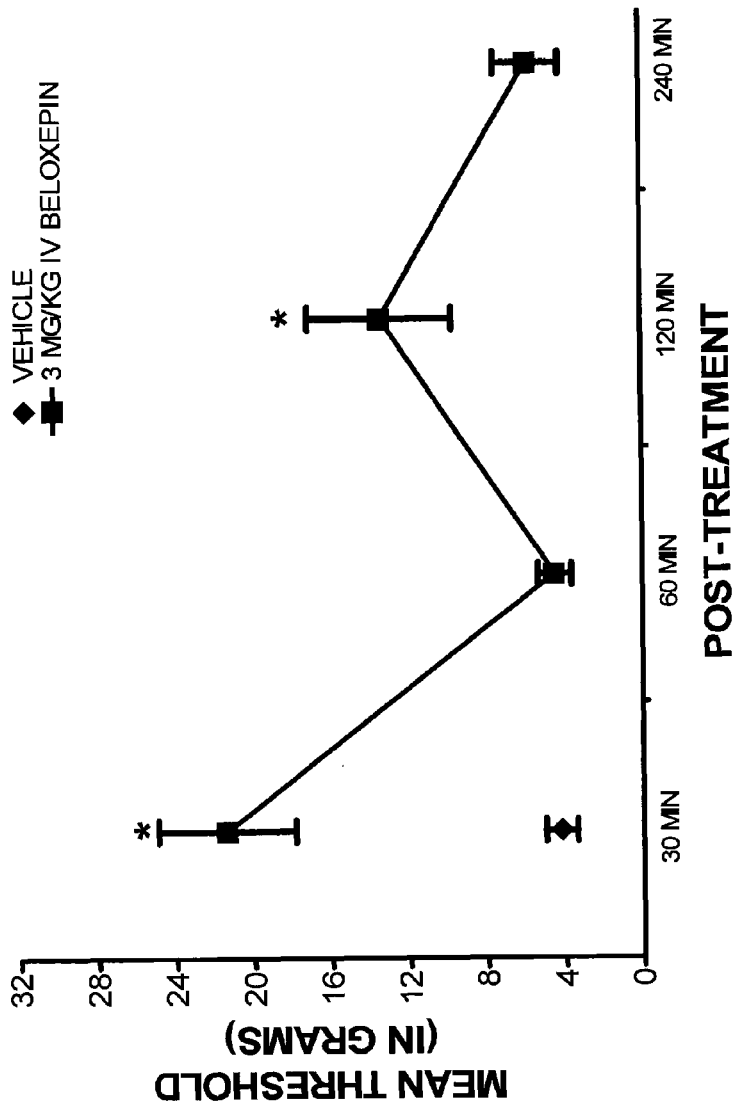

FIG. 1 provides a graph demonstrating the antiallodynic effect of beloxepin (30 mg/kg IP) in L5 SNL rats 14 days post surgery;

FIG. 2 provides a graph demonstrating the antiallodynic effect of beloxepin (3, 10 and 30 mg/kg IP) in L5 SNL rats 16 days post surgery;

FIG. 3 provides a graph illustrating the superior antiallodynic effect of beloxepin (30 mg/kg IP) as compared to reboxetine, a selective norepinephrine reuptake inhibitor (30 mg/kg IP), in L5 SNL rats;

FIG. 4 provides a graph demonstrating the antiallodynic effect of orally administered beloxepin (60 mg/kg PO) in L5 SNL rats 8 days post surgery;

FIG. 5 provides a graph comparing the antiallodynic effects produced by beloxepin, duloxetine, amitriptyline, and reboxetine (each at a concentration of 30 mg/kg IP) in L5 SNL rats;

FIGS. 6A and 6B provide graphs demonstrating the robust anti-nociceptive activity of beloxepin in a rodent model of acute nociception;

FIG. 7 provides a graph illustrating the robust antihyperalgesia activity of beloxepin in an animal model of inflammatory pain (rats treated with Freund's Complete Adjuvent);

FIG. 8 provides a graph illustrating the robust activity of beloxepin in a rodent model of visceral pain (mice treated with acetic acid);

FIG. 9 provides a graph comparing the mechanical antihyperalgesic effects of (30 mg/Kg IP) (±)-beloxepin and a reconstituted equimolar (racemic) mixture (30 mg/Kg IP) of (+)-beloxepin and (−)-beloxepin, in FCA-treated rats, 24 hours after FCA injection;

FIG. 10 provides a graph demonstrating the antiallodynic effect of orally administered beloxepin (60 mg/kg PO) in L5 SNL rats 7 days post surgery;

FIG. 11 provides a graph comparing the antiallodynic effects of beloxepin, duloxetine, and esreboxetine (each compound dosed at 30 mg/kg IP) in L5 SNL rats;

FIG. 12 provides a graph demonstrating the antiallodynic effect of beloxepin (30 mg/kg IP) in the rat hindpaw incisional model 24 hours post surgery;

FIG. 13 provides a graph demonstrating the antiallodynic effect of orally-administered beloxepin (60 mg/kg IP) in the rat hindpaw incisional model 24 hours post surgery; and FIG. 14 provides a graph demonstrating the antiallodynic effect of intravenously-administered beloxepin (3 mg/kg IV) in the rat hindpaw incisional model 24 hours post surgery.

Figure 15:
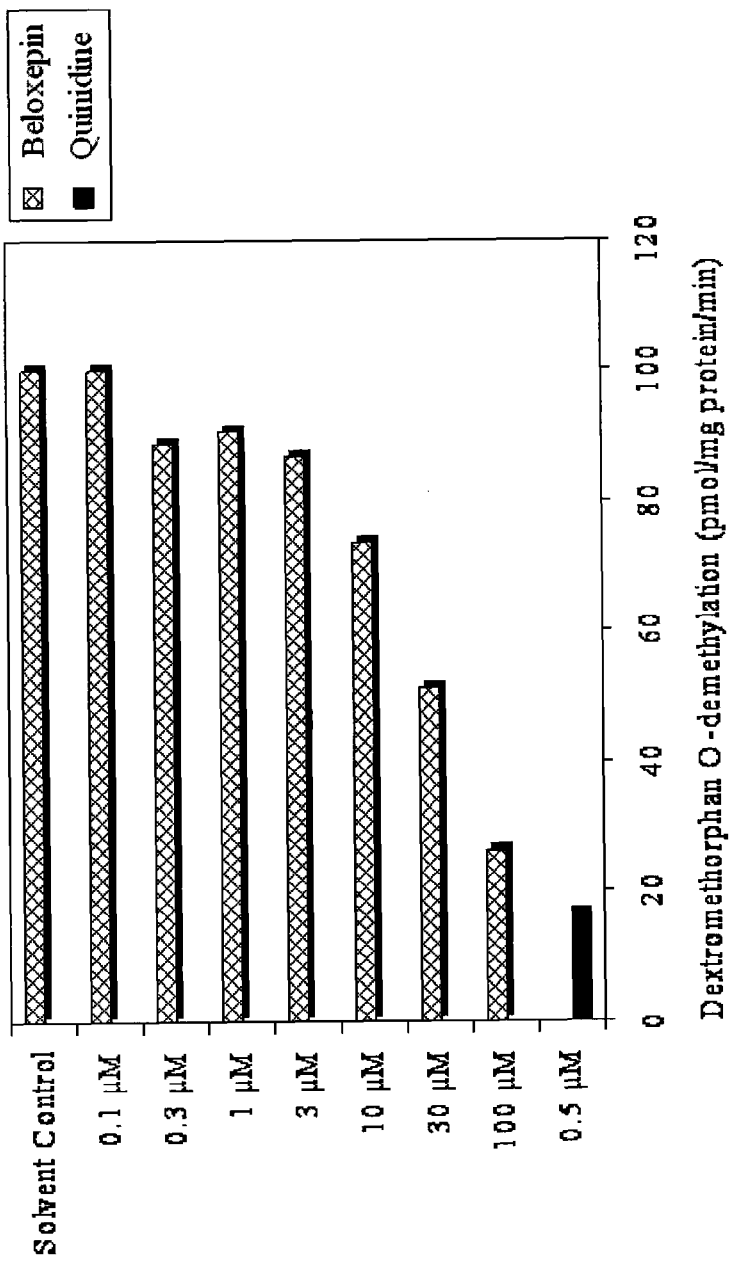

FIG. 15 provides a graph illustrating the inhibition of CYP2D6 (dextromethorphan O-demethylation) by beloxepin and quinidine.

8. DETAILED DESCRIPTION

The present disclosure concerns the use of beloxepin and/or its analogs to treat pain. The disclosure is based, in part, on the surprising discovery that beloxepin, which is a weak selective inhibitor of NE reuptake, nonetheless produces significant and robust activity across a broad spectrum of rodent models of various types of pain syndromes, including rodent models of acute nociceptive pain, inflammatory pain, visceral pain and neuropathic pain. As discussed in the Summary, inhibition of NE reuptake correlates with efficacy in the treatment of pain (see, Max et al., 1992, supra; Collins et al., 2000, supra; Atkinson et al., 1999, supra; Levental et al., 2007, supra). Based on its weak activity at the NET, beloxepin would not be expected to be useful in treating pain. Yet, it produces robust activity in numerous animal models of pain, and in the case of tactile anitallodynia, activity of magnitude greater than that observed with numerous compounds known to be effective in treating pain.

8.1 Beloxepin Compounds and Compositions

Beloxepin, also known as "Org-4428" and "cis-1,2,3,4,4a,13b-hexahydro-2,10-dimethyldiben-[2,3:6,7]oxepino[4,5c]pyridine-4a-ol]," is illustrated below:

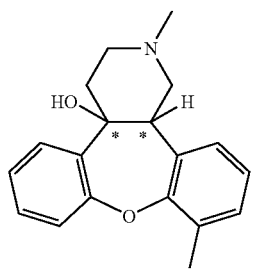

The OH and H substituents attached to the carbon atoms marked with asterisks are in the cis configuration with respect to one another. Since these carbons are chiral, this cis geometric isomer is a racemic mixture of two enantiomers, a (+) enantiomer and a (−) enantiomer. The absolute configurations about the chiral carbons of these (+) and (−) enantiomers are not presently known.

Analogs of beloxepin have been reported in the art. For example, U.S. Pat. No. 4,977,158, the disclosure of which is incorporated herein by reference, discloses beloxepin analogs according to structural formula (I):

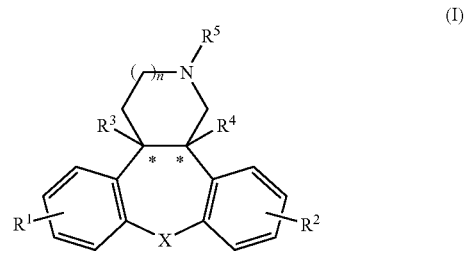

(I)

wherein:

n is 0 or 1;

X is O or S;

$R^1$ represents one or two identical or different substituents selected from H, OH, halogen, $C_1$-$C_4$ alkyl and $C_1$-$C_4$ alkoxy;

$R^2$ represents one or two identical or different substituents selected from H, OH, halogen, $C_1$-$C_4$ alkyl and $C_1$-$C_4$ alkoxy;

$R^3$ and $R^4$ are two substituents which are in the cis configuration, where $R^3$ is OH and $R^4$ is H; and $R^5$ is H or $C_1$-$C_4$ alkyl.

These analogs are expected to have biological and pharmacological properties similar to beloxepin, and are therefore also expected to be effective in treating and managing various pain syndromes as described herein. Beloxepin analogs according to structural formula (I) are referred to herein as "beloxepin analogs," or other grammatical equivalents. Thus, the beloxepin analogs can be used in the various compositions and methods described herein and the various illustrative embodiments described for beloxepin apply also to the beloxepin analogs as if such embodiments were specifically described.

Beloxepin and/or its analogs can be used in the various methods described herein as the compound per se, or can be included in a composition formulated for, among other things, a specific mode of administration. The beloxepin or beloxepin analog can be present in the composition as the free base, or in the form of a salt, for example, an acid additional salt. In some embodiments, such salts are pharmaceutically acceptable salts.

Generally, "pharmaceutically acceptable salts" are those salts that retain substantially one or more of the desired pharmacological activities of the parent compound and which are suitable for administration to humans. Pharmaceutically acceptable salts include, but are not limited to, acid addition salts formed with inorganic or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

8.2 Methods of Synthesis

Beloxepin and beloxepin analogs can be synthesized or prepared using methods described in the literature, for example, as described in U.S. Pat. No. 4,977,158, the disclosure of which is incorporated herein by reference. A specific method for synthesizing beloxepin that can be routinely adapted to synthesize beloxepin analogs, the details of which are discussed in the Examples section, is illustrated in Scheme 1, below:

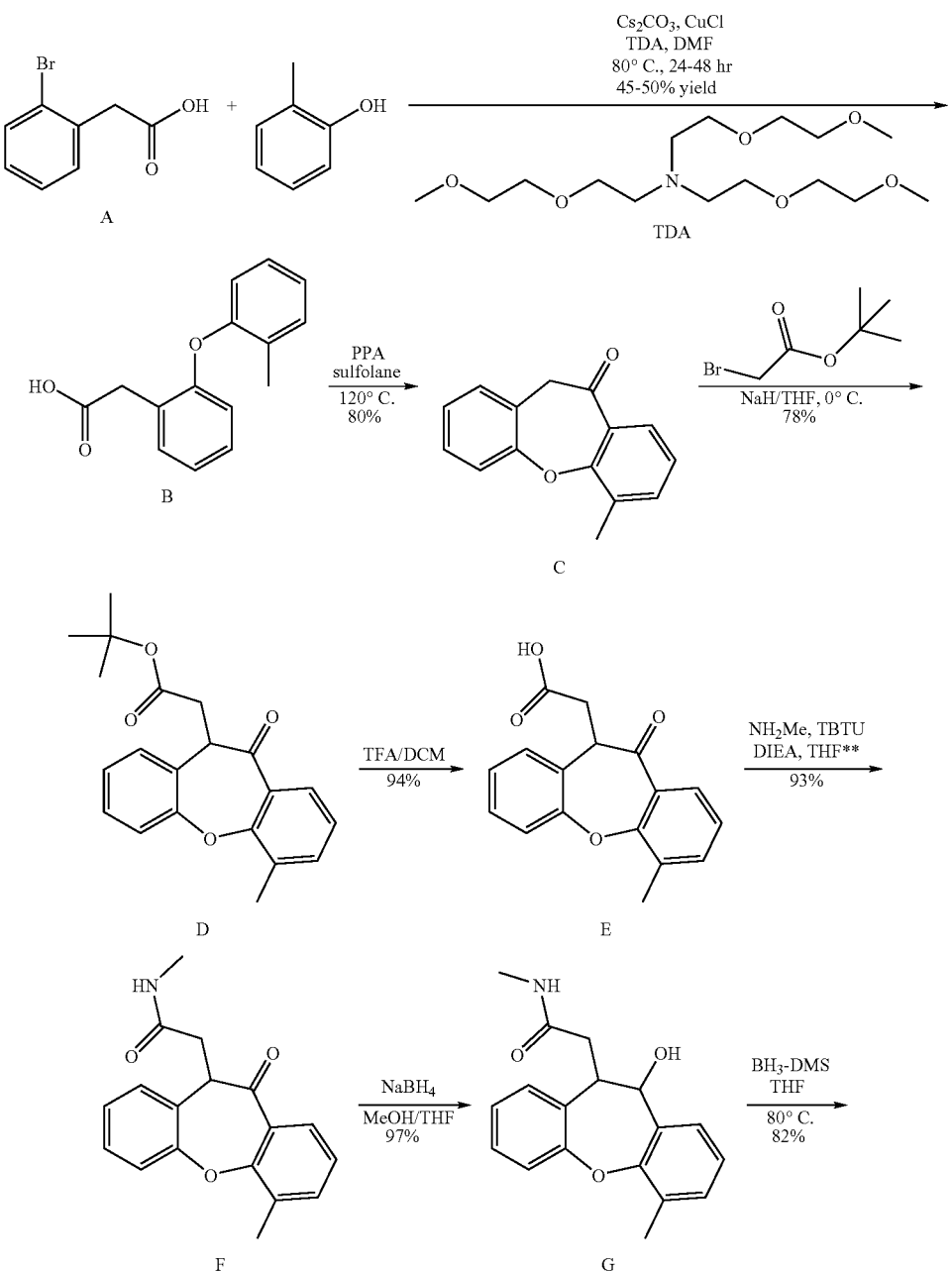

-continued

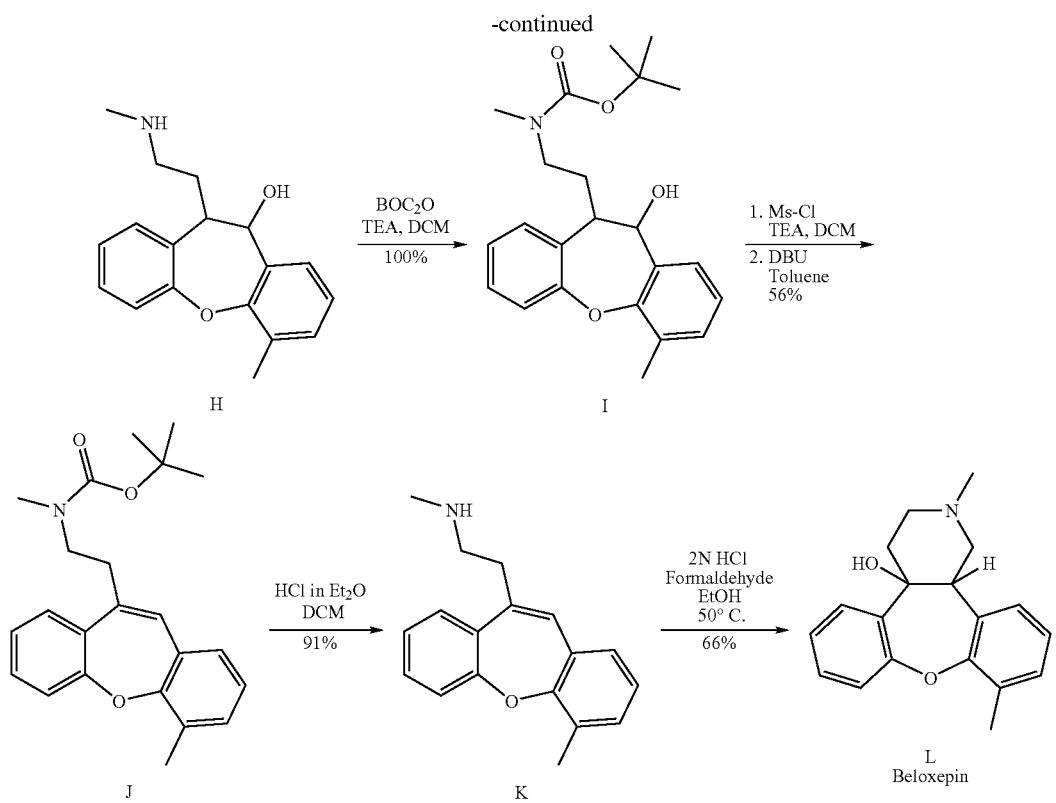

8.3 Uses of Beloxepin and its Analogs

Pain is generally understood to refer to the perception or condition of unpleasant sensory or emotional experience, which may or may not be associated with actual damage to tissues. It is generally understood to include two broad categories: acute and chronic (see, e.g., *Analgesics*, Buschmann et al., Wiley-VCH, Verlag GMbH & Co. KgaA, Weinheim, 2002; Jain, 2000, Emerging Drugs 5(2):241-257) that is either of nociceptive origin (for example somatic or visceral) or non-nociceptive origin (for example neuropathic or sympathetic). Acute pain generally includes nociceptive pain arising from strains/sprains, burns, myocardial infarction, acute pancreatitis, surgery, trauma and cancer. Chronic pain generally includes nociceptive pain, including, but not limited to, inflammatory pain such as that associated with IBS or rheumatoid arthritis, pain associated with cancer and pain associated with osteoarthritis; and non-nociceptive pain, including, but not limited to, neuropathic pain such as post-herpetic neuralgia, trigeminal neuralgia, focal peripheral nerve injury, anesthesia clolorosa, central pain (for example, post-stroke pain, pain due to spinal cord injury or pain associated with multiple sclerosis), and peripheral neuropathy (for example, diabetic neuropathy, inherited neuropathy or other acquired neuropathies).

Data presented in the Examples section confirm that beloxepin is surprisingly effective at treating pain in rodent models of neuropathic, acute nociceptive, inflammatory and visceral pain. Based upon this animal data, it is expected that beloxepin and beloxepin analogs will be useful in treating various different pain syndromes including, but not limited to, acute pain of nociceptive origin, such as, for example, surgical pain, chronic pain of nociceptive origin, such as, for example, inflammatory pain or cancer pain, and chronic pain of non-nociceptive origin, such as, for example, neuropathic pain.

In general, a "therapeutically effective" amount of a compound or composition is an amount that eradicates or ameliorates the underlying disease or indication being treated and/or that eradicates or ameliorates one or more of the symptoms associated with the underlying disorder such that the patient reports an improvement in feeling or condition, not withstanding that the patient may still be afflicted with the underlying disease or indication. Therapeutic benefits also includes halting or slowing the progression of the disease or indication, regardless of whether improvement is realized.

In the context of pain, a therapeutically effective amount is an amount of compound or composition that eradicates or ameliorates the pain or the symptoms thereof, including, but not limited to, shooting sensations, burning sensations, electrical sensations, aching, discomfort, soreness, tightness, stiffness, sleeplessness, numbness, and weakness.

The therapy can be applied following the onset of pain and/or one or more of its symptoms, or prophylactically to avoid or delay its onset.

8.4 Combination Therapies

Beloxepin and/or its analogs can be used alone, or in combination with, or adjunctively to, other therapeutic agents to treat pain.

Accordingly, beloxepin and/or its analogs can be combined with other analgesics, including but not limited to, cannabinoids and opioids. A number of cannabinoids are available that may be suitable for use in combination therapy, including, but not limited to, a cannabinoid that is selected from a $\Delta^9$-tetrahydrocannabinol and cannabidiol, and mixtures thereof.

Alternatively, beloxepin and/or its analogs may be used in combination with at least one opioid. A wide variety of opioids are available that may be suitable for use in combination therapy to treat pain. As such, the combination therapy may involve an opioid that is selected from, but not limited to, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papavereturn, pentazocine, phenadoxone, phenomorphan, phanazocine, phenoperidine, piminodine, piritramide, propheptazine, promedol, properidine, propiram, propoxyphene, sulfentanil, tilidine, tramadol, diastereoisomers thereof, pharmaceutically acceptable salts thereof, complexes thereof; and mixtures thereof. In some embodiments, the opioid is selected from morphine, codeine, oxycodone, hydrocodone, dihydrocodeine, propoxyphene, fentanyl, tramadol, and mixtures thereof.

The opioid component of the combination therapy may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference*, 1999, the disclosure of which is hereby incorporated herein by reference, in its entirety.

The opioid component may further include one or more compounds that may be designed to enhance the analgesic potency of the opioid and/or to reduce analgesic tolerance development. Such compounds include, for example, dextromethorphan or other NMDA antagonists (Mao et al., 1996, Pain 67:361), L-364,718 and other CCK antagonists (Dourish et al., 1988, Eur. J. Pharmacol 147:469), NOS inhibitors (Bhargava et al., 1996, Neuropeptides 30:2), PKC inhibitors (Bilsky et al., 1996, J. Pharmacol. Exp. Ther. 277:484), and dynorphin antagonists or antisera (Nichols et al., 1997, Pain 69:317). The disclosures of each of the foregoing documents are hereby incorporated herein by reference, in their entireties.

Alternatively, beloxepin and/or its analogs may be used with at least one non opioid analgesic, such as for example, diclofenac, a COX2 inhibitor, aspirin, acetaminophen, ibuprofen, naproxen, and the like, and mixtures thereof.

Other agents that may be used in combination with the beloxepin and/or its analogs include anti-inflammatories. Specific examples of suitable anti-inflammatories include, but are not limited to, corticosteroids, aminoarylcarboxylic acid derivatives such as, but not limited to, etofenamate, meclofenamic acid, mefenamic acid, niflumic acid; arylacetic acid derivatives such as, but not limited to, acemetacin, amfenac cinmetacin, clopirac, diclofenac, fenclofenac, fenclorac, fenclozic acid, fentiazac, glucametacin, isozepac, lonazolac, metiazinic acid, oxametacine, proglumetacin, sulindac, tiaramide and tolmetin; arylbutyric acid derivatives such as, but not limited to, butibufen and fenbufen; arylcarboxylic acids such as, but not limited to, clidanac, ketorolac and tinoridine; arylpropionic acid derivatives such as, but not limited to, bucloxic acid, carprofen, fenoprofen, flunoxaprofen, ibuprofen, ibuproxam, oxaprozin, piketoprofen, pirprofen, pranoprofen, protizinic acid and tiaprofenic add; pyrazoles such as, but not limited to, mepirizole; pyrazolones such as, but not limited to, clofezone, feprazone, mofebutazone, oxyphenbutazone, phenylbutazone, phenyl pyrazolidininones, suxibuzone and thiazolinobutazone; salicylic acid derivatives such as, but not limited to, bromosaligenin, fendosal, glycol salicylate, mesalamine, 1-naphthyl salicylate, olsalazine and sulfasalazine; thiazinecarboxamides such as, but not limited to, droxicam, isoxicam and piroxicam; and other anti-inflammatory agents such as, but not limited to, e-acetamidocaproic acid, s-adenosylmethionine, 3-amino-4-hydroxybutyric acid, amixetrine, bendazac, bucolome, carbazones, difenpiramide, ditazol, guaiazulene, heterocyclic aminoalkyl esters of mycophenolic acid and derivatives, nabumetone, nimesulide, orgotein, oxaceprol, oxazole derivatives, paranyline, pifoxime, 2-substituted-4,6-di-tertiary-butyl-s-hydroxy-1,3-pyrimidines, proquazone and tenidap.

Beloxepin and its analogs can also be used in combination with each other. Thus, in some embodiments, the combination therapy involves administration of two or more beloxepin analogs, or beloxepin and one or more beloxepin analogs.

8.5 Additional Properties of Beloxepin

As indicated in Example 3, an initial, screening study suggested that beloxepin inhibits the polymorphic cytochrome P450 isoenzyme CYP2D6 ($IC_{50}$=536 nM). A subsequent, more definitive analysis in which CYP2D6 inhibition by beloxepin was measured human hepatic microsomes using dextromethorphan as the model. There, beloxepin caused direct inhibition of CYP2D6 with an $IC_{50}$ value of only 31.7 µM (FIG. 15), indicating that, CYP inhibition would therefore be negligible for beloxepin. Cytochrome P450 enzymes play important roles in drug metabolism. For example, many tricyclic antidepressants used off-label to treat pain are metabolized by CYP2D6. Use of inhibitors of this enzyme in combination therapy regimens can therefore dramatically increase their levels. Co-administration of CYP2D6 inhibitors with substrates of CYP2D6 can also prolong the QT interval, leading to arrythmias.

Certain prodrugs are acted upon by CYP2D6 to release the active drug. CYP2D6 inhibitors would likely reduce the efficacy of such CYP2D6-activated drugs. As a specific example, clinical evidence suggest that CYP2D6-activated prodrugs such as codeine and tramadol are less effective in patients who are genetically deficient in CYP2D6 or in patients receiving potent CYP2D6 inhibitors.

Cytochrome P4502D6 (CYP2D6) is a polymorphic member of the P450 superfamily, which is absent in 5-9% of the Caucasian population, resulting in a deficiency in drug oxidation known as debrisoquine/sparteine polymorphism. Metabolism by polymorphic isoenzymes such as CYP2D6 can be problematic in drug development because of the wide variation in the pharmacokinetics of the patient population. CYP2D6 metabolises many currently used drugs, which include β-blockers, antidepressants, and neuroleptics (Bertz and Granneman, 1997, Clin. Pharmokinet 32(3):210-58). Polymorphisms of 2D6 have been associated with a reduced capacity to dispose important drugs; this leads to undesirable clinical consequences (Ingelman-Sundberg et al., 1999, Trends. Pharmacol. Sci. 20(8):342-349). The impact of human P450 polymorphisms on drug treatment in poor metabolizers is indicated in Table 1 below (Ingelman-Sundberg et al., 1999, Trends. Pharmacol. Sci. 20(8):342-349).

TABLE 1

Impact of human P450 polymorphisms on drug treatment in poor metabolizers

| Polymorphic enzyme | Decreased clearance | Adverse effects | Reduced prodrug activation |
|---|---|---|---|
| CYP 2C9 | S-Warfarin | Bleeding | Losartan |
| | PHenytoin | Ataxia | |
| | Losartan | | |
| | Tolbutamide | Hypoglycaemia | |
| | NSAIDs | GI bleeding | |
| CYP 2C19 | Omeprazole | | Proguanil |
| | Diazepam | Sedation | |
| CP2D6 | Tricyclic antidepressants | Cardiotoxicity | Tramadol Codeine |
| | Haloperidol | Parkinsonism | Ethylmorphine |
| | Anti-arrhythmic drugs | Arrhythmias | |
| | Perphenazine | | |
| | Perhexiline | Neuropathy | |
| | SSRIs | Nausea | |
| | Zuclopenthixol | | |
| | S-Mianserin | | |
| | Tolterodine | | |

Abbreviations: NSAIDs, nonsteroidal anti-inflammatory drugs; SSRIs, selective serotonin reuptake inhibitors Thus, in view of the above and the data of Example 3, skilled artisans will appreciate that in the various combination therapies discussed herein, dosages may need to be adjusted when beloxepin and/or its analogs are administered in combination with, or adjunctively to, drugs that are either metabolized by or activated by, CYP2D6.

As indicated above, preliminary screening assays for inhibition of cDNA-expressed human CYP450 isozymes by beloxepin at 10 μM, suggested extensive inhibition of CYP2D6 (97%). The potential inhibition of CYP2D6 was re-evaluated using dextromethorphan as the model substrate, and measuring inhibition of CYP2D6 by beloxepin in human hepatic microsomes. In these definitive studies, beloxepin caused direct inhibition of CYP2D6 with an $IC_{50}$ value of 31.7 μM (FIG. 15). At anticipated therapeutic plasma concentrations, CYP inhibition would therefore be negligible for beloxepin. This suggests that beloxepin has little potential for drug-drug interactions.

8.6 Formulations and Administration

Beloxepin and/or its analogs (or salts thereof) may be combined with a pharmaceutical carrier selected on the basis of the chosen route of administration and standard pharmaceutical practice as described, for example, in *Remington's Pharmaceutical Sciences*, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

The compositions may be formulated for oral administration, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations may be prepared so that an oral dosage unit form contains from about 0.1 to about 1000 mg of each beloxepin enantiomer (and all combinations and subcombinations of ranges and specific concentrations therein).

The tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the dosage unit form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non toxic in the amounts employed.

The compositions may also be formulated for parenteral or intraperitoneal administration. Solutions of the beloxepin enantiomers as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

Compositions suitable for administration by injection typically include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile filtered solution thereof.

8.7 Effective Dosages

Beloxepin and/or beloxepin analogs will generally be administered in a therapeutically effective amount, as described herein. The quantity of beloxepin and/or beloxepin analog compounds will depend upon a variety of factors, including, for example, the particular pain indication or syndrome being treated, the mode of administration, whether the desired benefit is prophylactic or therapeutic, the severity of the pain indication or syndrome being treated, the age and weight of the patient, and the bioavailability of beloxepin and/or beloxepin analog(s) administered. Determination of an effective dosage is well within the capabilities of those skilled in the art.

Dosage amounts will typically be in the range of from about 0.0001 or 0.001 or 0.01 mg/kg/day total active compound(s) to about 0.1 or 1.0 or 2.0 or 2.5 or 5.0 or 10.0 or 20.0 or 25.0 or 50.0 or 75.0 or 100 mg/kg/day total active compound(s), with an expected dose of about 5 mg/kg/day to about 1500 mg/kg/day total active compound(s), but may be higher or lower, depending upon, among other factors, the factors mentioned above.

Dosage amount and interval may be adjusted individually to provide plasma levels of active compound(s), which are sufficient to maintain therapeutic or prophylactic effect. As non-limiting examples, the compositions may be administered once per day or multiple times per day, depending upon, among other things, the mode of administration, the specific indication being treated and the judgment of the prescribing physician. In cases of local administration or selective uptake, such as local topical administration, the effective local concentration of active compounds and/or compositions may not be related to plasma concentration. Skilled artisans will be able to optimize effective local dosages without undue experimentation.

Based on the animal data described in the Examples section, it is expected that an effective dosage of beloxepin for the treatment of pain in humans may be obtained by administering a dose of beloxepin sufficient to achieve a plasma concentration similar to that achieved following the administration of 30 mg/kg, i.p. to rats, or 60 mg/kg PO to rats. As such, in some embodiments the effective dose of beloxepin for the treatment of pain is the dosage required to achieve the plasma concentration achieved when 30 mg/kg beloxepin is administered i.p. to rats, or when 60 mg/kg beloxepin is administered orally to rats.

Based on these animal data, it is expected that oral doses of beloxepin of between about 10 mg/day to about 20 or 25 or 30 or 35 or 40 or 45 or 50 or 60 or 70 or 80 or 90 or 95 or 100 or 200 or 500 or 750 or 1000 or 1500 mg/day will be effective in treating pain. Accordingly, some embodiments involve the administration of an oral dosage of beloxepin that ranges from about 10 mg/day to about 500 mg per dose, one or more times per day. It is expected that similar dosage ranges of beloxepin analogs will be effective.

In the context of combination therapy, the proper dosage of the combined agents will be readily ascertainable by a skilled artisan based on long established criteria. By way of general guidance, where a cannabinoid, opioid and/or other agent is used in combination with beloxepin, the dosage will typically range from about 0.01 to about 100 mg/kg/day of the cannabinoid, opioid and/or other active compound and about 0.001 to about 100 mg/kg/day of beloxepin. In certain embodiments, the dosage may be about 0.1 to about 10 mg/kg/day of the cannabinoid, opioid and/or other active compound and about 0.01 to about 10 mg/kg/day of beloxepin, and in other embodiments, the daily dosage may be about 1.0 mg of the cannabinoid, opioid and/or other active compound and about 0.1 mg of beloxepin. Alternatively, when beloxepin is combined with a cannabinoid compound (e.g., $\Delta^9$-tetrahydrocannabinol or cannabidiol), an opioid compound (e.g., morphine) and/or an other agent and the combination is administered orally, the dosage may generally range from about 15 to about 200 mg of the cannabinoid, opioid and/or other agent, and about 0.1 to about 4 mg of beloxepin. It is expected that similar dosage ranges will be effective for combination therapies with beloxepin analogs.

8.8 Kits

Beloxepin and/or beloxepin analogs may be assembled in the form of kits. In some embodiments, the kit provides the compounds(s) and reagents to prepare a composition for administration. The composition may be in a dry or lyophilized from, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to, syringe, pipette, transdermal patch or inhalant.

The kits may include other therapeutic agents for use in conjunction with the compositions described herein. In some embodiments, the therapeutic agents may be provided in a separate form, or mixed with the compositions described herein.

Kits can include appropriate instructions for preparation and administration of the composition, side effects of the compositions, and any other relevant information. The instructions may be in any suitable format; including, but not limited to, printed matter, videotape, computer readable disk, or optical disk.

9. EXAMPLES

The following working examples, which are intended to be illustrative and not limiting, highlight various features of beloxepin and certain uses described herein.

Example 1

Synthesis of (±)-Beloxepin

With reference to Scheme 1, reproduced below, beloxepin was synthesized as follows.

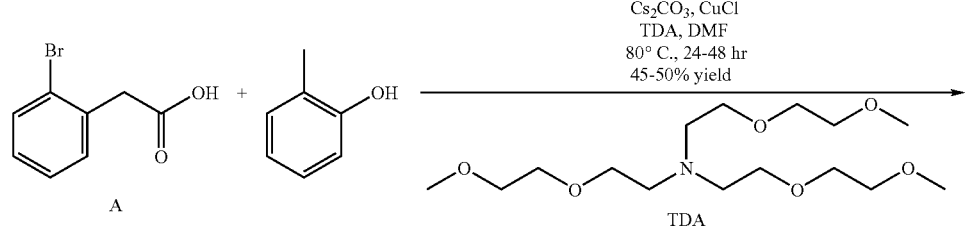

-continued
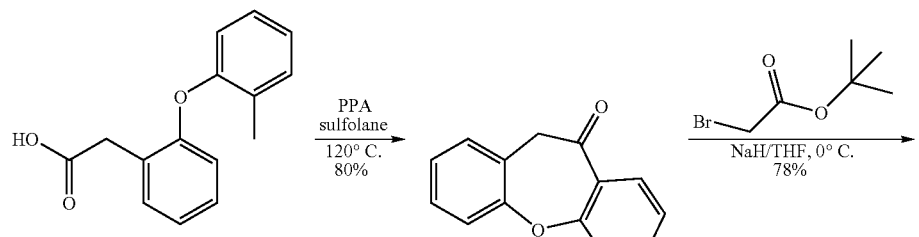
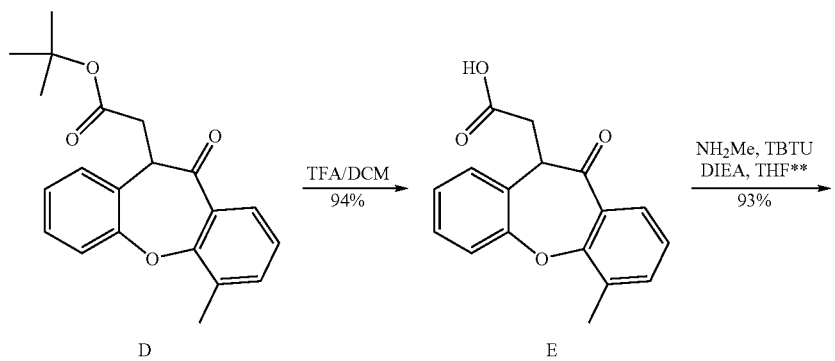
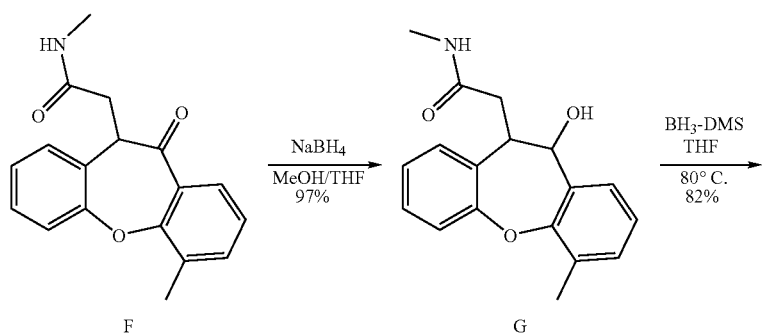
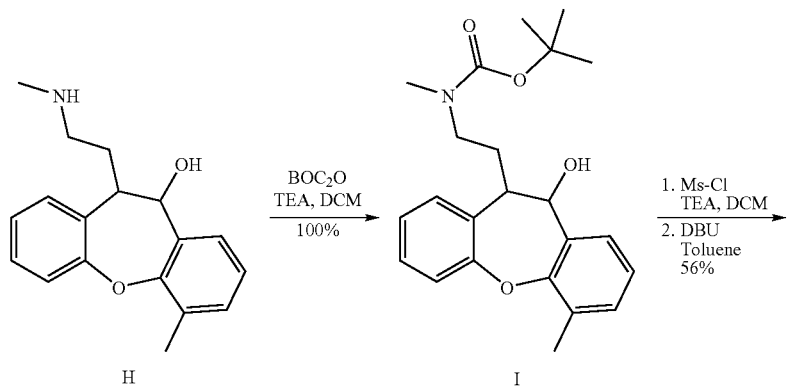

-continued

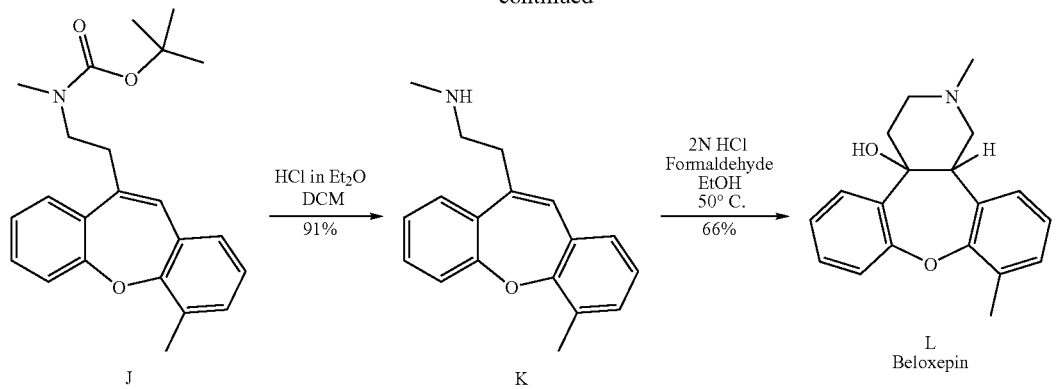

J → K → L Beloxepin

Preparation of 2-(2-(o-tolyloxy)phenyl)acetic acid (B): To a solution of A (50.0 g, 232 mmol, 1.00 eq) in N,N-dimethylformamide (500 mL) under nitrogen and with mechanical stirring was added cesium carbonate (189 g, 581 mmol, 2.50 eq), o-cresol (28.8 mL, 279 mmol, 1.20 eq), copper(I) chloride (12 g, 120 mmol, 0.5 eq) and tris(3,6-dioxaheptyl)amine (TDA) (37 mL, 120 mmol, 0.5 eq). The reaction was degassed by bubbling nitrogen through the stirring mixture for 10 minutes. The mixture was then heated at 80° C. for 2 days under nitrogen. The reaction was cooled to room temperature and diluted with 1:1 diethyl ether/hexanes. While stirring, the mixture was carefully acidified with 6M HCl, then diluted with water and the layers were separated. The aqueous layer was washed with 1:1 diethyl ether/hexanes and all organics were combined and washed with 0.5M sodium carbonate. The basic aqueous layers were combined, acidified with 6M HCl and the product was extracted with diethyl ether. The organics were concentrated and purified by a silica gel plug using 2-5% isopropanol/hexane gradient to give 31.48 g yellow/green oil (51% yield, based on $^1$H NMR purity of 92%). $^1$H NMR (400 MHz, CDCl$_3$) 7.29 (dd, 1H), 7.23-7.10 (m, 3H), 7.05 (m, 2H), 6.83 (dd, 1H), 6.63 (dd, 1H), 3.77 (s, 2H), 2.20 (s, 3H); MS: (M−H)$^-$=241.1.

Preparation of 6-methyldibenzo[b,f]oxepin-10(11H)-one (C): A mixture of B (60.7 g, 213 mmol, 1.00 eq, 85% purity), polyphosphoric acid (93 g, 852 mmol, 4.00 eq) and sulfolane (200 mL) was immersed in an oil bath at 120° C. and heated for 90 minutes. Ice water was added and the product was extracted with diethyl ether. The organic layer was washed with 0.5 M sodium carbonate, concentrated and purified by a silica gel plug using a 1-4% ethyl acetate/hexanes gradient to give 41.4 g orange oil (80%). Yield based on 85% purity of starting material B and 92% purity of product C. $^1$H NMR (400 MHz, CDCl$_3$) 7.91 (m, 1H), 7.44 (m, 1H), 7.32 (m, 1H), 7.25 (m, 2H), 7.19 (m, 1H), 7.07 (m, 1H), 4.10 (s, 2H), 2.57 (s, 3H)

Preparation of (4-Methyl-1'-oxo-10,11-dihydro-dibenzo[b,f]oxepin-10-yl)-acetic acid tert-butyl ester (D): To a mixture of 60% sodium hydride in mineral oil (8.16 g, 204 mmol, 1.2 eq) in tetrahydrofuran (400 mL) cooled in a brine/water bath was added dropwise a solution of the ketone C (41.4 g, 170 mmol, 1.0 eq, 92% purity) in tetrahydrofuran (200 mL). The mixture was stirred for an additional 10 minutes. The bromide was added dropwise over a 10 minutes period and the reaction was stirred cooled for 40 minutes. The reaction was quenched with water and concentrated. The crude product was partitioned between water and diethyl ether, layers were separated and the organics were washed with brine. The organics were concentrated and the resulting solid was triturated in hexanes, filtered and dried to give 44.1 g of an off-white solid. The filtrate was concentrated and there were crystals after 3 days. Crystals were filtered and dried to give 1.5 g pale orange crystalline solid. Total yield=78%. $^1$H NMR (400 MHz, CDCl$_3$) 7.86 (dd, 1H), 7.43 (m, 1H), 7.25-7.20 (m, 4H), 7.06 (t, 1H), 4.83 (m, 1H), 3.37 (m, 1H), 2.87 (dd, 1H), 2.57 (s, 3H), 1.42 (s, 9H); MS: M=338.4

Preparation of (4-Methyl-1'-oxo-10,11-dihydro-dibenzo[b,f]oxepin-10-yl)-acetic acid (E): The ester D (44.0 g, 128 mmol, 1.0 eq) was dissolved in dichloromethane (500 mL) and trifluoroacetic acid (34.5 mL, 448 mmol, 3.5 eq) was added. The reaction was stirred at room temperature over 48 h. The reaction was diluted with water and the layers were separated. The organics were concentrated, triturated in 1:1 diethyl ether/hexanes (250 mL), filtered and dried to give 34.6 g of a pale yellow solid (94%). $^1$H NMR (400 MHz, DMSO) 12.40 (brs, 1H), 7.72 (dd, 1H), 7.61 (m, 1H), 7.44 (m, 1H), 7.36-7.30 (m, 3H), 7.18 (t, 1H), 4.73 (m, 1H), 3.33 (m, 1H), 2.92 (dd, 1H), 2.57 (s, 3H); MS: (M−H)$^-$=281.2

Preparation of N-Methyl-2-(4-methyl-1'-oxo-10,11-dihydro-dibenzo[b,f]oxepin-10-yl)-acetamide (F): The acid E (34.5 g, 120 mmol, 1.0 eq) was suspended in tetrahydrofuran (200 mL) under nitrogen. To the mixture was added N,N-diisopropylethylamine (31.3 mL, 180 mmol, 1.5 eq), methyl amine (120 mL, 240 mmol, 2.0 eq) and TBTU (46.2 g, 144 mmol, 1.2 eq). The reaction was stirred at room temperature for 2 hours. Between 30 and 60 minutes, a thick precipitate forms and the reaction turns light green. Another 100 mL of tetrahydrofuran was added and slow stirring resumed. N,N-dimethylformamide (100 mL) was added followed by additional amount of TBTU (15 g). The reaction mixture was concentrated to near dryness and the product was partitioned between diethyl ether and a 50% aqueous solution of sodium bicarbonate. The aqueous was washed with diethyl ether and all organics were combined and concentrated. The resulting solid was triturated in 300 mL 1:1 diethyl ether/hexanes, filtered and dried to give 33.3 g off-white solid (93%). $^1$H NMR (400 MHz, CDCl$_3$) 7.84 (dd, 1H), 7.43 (m, 1H), 7.25-7.20 (m, 3H), 7.16 (m, 1H), 7.06 (t, 1H), 4.96 (dd, 1H), 3.33 (m, 1H), 2.82 (d, 3H), 2.75 (dd, 1H), 2.57 (s, 3H); MS: (M+H)$^+$=296.0

Preparation of 2-(11-Hydroxy-4-methyl-10,11-dihydro-dibenzo[b,f]oxepin-10-yl)-N-methyl-acetamide (G): The ketone F (33.2 g, 112 mmol, 1.0 eq) was partially dissolved in methanol/tetrahydrofuran (200 mL/200 mL) under nitrogen and cooled in an ice/water bath. Sodium borohydride (10.6 g, 281 mmol, 2.5 eq) was added in 2 g portions over a 15 minutes period. The ice bath was removed and the mixture was stirred at room temperature for 1 hour. The reaction was quenched with water and concentrated to near dryness. The crude product was suspended in dichloromethane, water was added and the layers were separated. The aqueous layer was washed again with dichloromethane and the organics were combined and concentrated. To the resulting foam was added 250 mL of 1:1 diethyl ether/hexanes with vigorous stirring. A white precipitate immediately formed and it was filtered and dried to give 32 g of a white powder (97%); MS: (M+H)$^+$=298.0

Preparation of 6-Methyl-11-(2-methylamino-ethyl)-10,11-dihydro-dibenzo[b,f]oxepin-10-ol (H): The amide G (31.9 g, 107 mmol, 1.0 eq) was dissolved in tetrahydrofuran (200 mL) under nitrogen and the borane-dimethyl sulfide complex (2.0 M in tetrahydrofuran, 161 mL, 322 mmol, 3.0 eq) was added dropwise over 15 minutes. The reaction was then heated at 80° C. for 24 hours. The reaction was cooled in an ice/water bath and methanol (50 mL) was added in 10 mL portions over 30 minutes. The mixture was stirred for 30 minutes at room temperature. A solution of 4M HCl in dioxane (130 mL, ~5 eq) was added dropwise over 15 minutes. The mixture was stirred at room temperature for 30 minutes. The mixture was concentrated to near dryness and water and 10% ethyl acetate/diethyl ether were added. Layers were separated and the aqueous phase was washed with 10% ethyl acetate/diethyl ether. The aqueous layer was basified with a saturated sodium bicarbonate solution and the product was extracted with 10% methanol/dichloromethane. The organics were combined, dried over sodium sulfate, concentrated and dried to give 25.8 g of a yellow oil (82%). MS: (M+H)$^+$=284.0

Preparation of [2-(11-hydroxy-4-methyl-10,11-dihydro-dibenzo[b,f]oxepin-10-yl)-ethyl]-methyl-carbamic acid tert-butyl ester (I): To a solution of the amine H (25.0 g, 86 mmol, 1.0 eq, 96.9% pure) and triethylamine (14.3 mL, 102 mmol, 1.2 eq) in dichloromethane (300 mL) was added di-tert-butyldicarbonate (19.6 g, 90 mmol, 1.05 eq) portion wise. The reaction was stirred at room temperature for 15 minutes. The reaction was diluted with 0.5 M HCl and the layers were separated. The organics were washed with 0.5 M HCl, dried over sodium sulfate, concentrated and dried to give 35 g of a yellow oil (100% yield based on 93% purity). MS: (M+H)$^+$=384.0

Preparation of methyl-[2-(4-methyl-dibenzo[b,f]oxepin-10-yl)-ethyl]-carbamic acid tert-butyl ester (J): The alcohol I (23.5 g, 57 mmol, 1.0 eq, 93% purity) was dissolved in dichloromethane (300 mL) and triethylamine (20.6 mL, 148 mmol, 2.6 eq) was added. The mixture was cooled in an ice bath and methanesulfonyl chloride (5.73 mL, 74 mmol, 1.3 eq) was added. The reaction mixture was stirred cooled for 15 minutes. The reaction mixture was diluted with 0.5 M HCl and the layers were separated. The organics were concentrated and dried to give 28 g of a crude light yellow oil. The mesylate was dissolved in toluene (200 mL) and 1,8-diazabicyclo[5.4.0]undec-7-ene (42.6 mL, 285 mmol, 5.0 eq) was added. The mixture was heated at 115° C. for 1 hour and diluted with water. The layers were separated and the organics were concentrated and purified by a silica gel plug eluting with 5-15% ethyl acetate/hexanes to give 14.76 g of a light yellow oil. This total amount was collected in two batches (8.44 g, 81% pure by LC/MS) and (6.32 g, 77% pure by LC/MS). $^1$H NMR (400 MHz, CDCl$_3$) 7.40 (brm, 1H), 7.28 (m, 1H), 7.22-7.10 (m, 3H), 6.98 (m, 2H), 6.70 (brs, 1H), 3.39 (brm, 2H), 2.91-2.82 (brm, 5H), 2.53 (s, 3H), 1.46 (s, 9H); MS: (M+H)$^+$=366.0

Preparation of methyl-[2-(4-methyl-dibenzo[b,f]oxepin-10-yl)-ethyl]-amine (K): The olefin J (14.8 g, 32 mmol, 1.0 eq, 79% pure) was dissolved in dichloromethane (150 mL) and a solution of HCl in diethyl ether (2.0M, 75 mL, 160 mmol, 5 eq) was added. The mixture was stirred overnight at room temperature. The reaction was diluted with a solution of saturated sodium bicarbonate and layers were separated. The aqueous layer was washed with 10% methanol/dichloromethane and all organics were combined, concentrated and purified by a flash silica gel column using a 2-10% methanol/dichloromethane gradient (plus 1% NH$_4$OH) to give 8.0 g of a yellow oil in 91% yield and 96% purity. $^1$H NMR (400 MHz, CDCl$_3$) 7.38 (m, 1H), 7.30 (m, 2H), 7.15 (m, 2H), 6.99 (m, 2H), 6.74 (s, 1H), 2.93 (t, 2H), 2.78 (t, 2H), 2.52 (s, 3H), 2.44 (s, 3H); MS: (M+H)$^+$=266.0

Preparation of Beloxepin (L): To the amine K (7.0 g, 25 mmol, 1.0 eq) under nitrogen was added ethanol (23 mL), an aqueous solution of HCl (2.0 M, 226 mL, 19 eq) and an aqueous solution of formaldehyde (37%, 100 mL, 52 eq). The reaction mixture was heated at 50° C. for 64 hours. The reaction mixture was cooled in an ice bath and it was basified with 2M NaOH to pH ~8. The product was extracted with 10% methanol/dichloromethane. The organics were combined, concentrated and purified by a flash silica gel column using a 4-9% methanol/dichloromethane gradient (plus 1% NH$_4$OH) to give 4.9 g white solid in 66% yield and 100% purity. $^1$H NMR (400 MHz, CDCl$_3$) 7.62 (d, 1H), 7.27 (m, 3H), 7.14 (m, 1H), 7.08 (m, 1H), 7.00 (m, 1H), 3.28 (brs, 1H), 3.10 (brt, 1H), 3.00 (brm, 1H), 2.82 (brm, 1H), 2.46 (brs, 1H), 2.42 (s, 3H), 2.29 (s, 3H), 2.18 (m, 1H), 2.03 (s, 1H), 1.80 (brm, 1H); MS: (M+H)$^+$=296.0. CHN Theory (1 mol H$_2$O): % C, 72.82% H, 7.40% N, 4.47. CHN Actual (1 mol H$_2$O): % C, 72.69% H, 7.29% N, 4.48

Preparation of reconstituted racemic mixture of beloxepin (see FIG. 9):

300 mg of (+)-Beloxepin and 300 mg of (−)-Beloxepin were combined and dissolved in 10 mL of hexanes/methanol (30:70). The solution was concentrated on a rotovap at 37° C. to give an off-white foam (Beloxepin lot 9). $^1$H NMR (400 MHz, CDCl$_3$) consistent for product. LC/MS: ESI+ M+=295.6; purity=100% RT=0.64; CHN Theory: % C, 77.26% H, 7.17% N, 4.74, CHN Found: % C, 77.04, 77.10% H, 7.17, 7.20% N, 4.77, 4.79

Example 2

Beloxepin is an Inhibitor of NE Reuptake

The binding affinities of beloxepin for the NE, serotonin and dopamine transporters were determined in competitive binding assays with radiolabeled ligands. The ability of beloxepin to inhibit reuptake of NE was also determined. It was observed that beloxepin had only marginal affinity for the serotonin transporter (27% inhibition of binding at 10 μM in a competition assay) and dopamine transporter (16% inhibition of binding at 10 μM in a competition assay). Other results observed are provided below.

Protocols. For the NE transporter binding assay, [$^3$H] nisoxetine (1.0 nM) was incubated with various concentrations of beloxepin for 2 hours at 4° C. with membranes prepared from Chinese hamster ovary cells (CHO) cells heterologously expressing the cloned human NE transporter (hNET). Bound radioactivity was determined by scintillation spectroscopy. Non-specific binding was defined as the amount of binding that occurred in the presence of 1.0 μM desipramine. The K$_i$ was determined using standard methods.

The IC$_{50}$ of NE reuptake inhibition was determined by measuring the degree to which various concentrations of beloxepin inhibited incorporation of [$^3$H]norepinephrine into rat hypothalamus synaptosomes (measurements carried out for 20 minutes at 37° C.).

For the 5HT transporter binding assay, [$^3$H]imipramine (2.0 nM) was incubated in the presence of various concentrations of beloxepin for 1 hour at 22° C. with membranes prepared from CHO cells heterologously expressing the human serotonin transporter (hSERT). Bound radioactivity was determined by scintillation spectroscopy. Non-specific binding was defined as the amount of binding that occurred in the presence of 10 μM imipramine. The $K_i$ was determined using standard methods.

The $IC_{50}$ of 5HT reuptake inhibition was determined by measuring the degree to which various concentrations of beloxepin inhibited incorporation of [$^3$H]-5HT into rat brain synaptosomes (measurements carried out for 15 min at 37° C.

For the DA transporter binding assay, [$^3$H]N-[1-(2-benzo[b]thiophenyl)cyclohexyl]-piperidine ([$^3$H]BTCP) (4.0 nM) was incubated in the presence of various concentrations of beloxepin for 2 hr at 4° C. with membranes prepared from Chinese hamster ovary (CHO) cells heterologously expressing the cloned human dopamine transporter (hDAT). Bound radioactivity was determined by scintillation spectroscopy. Non-specific binding was defined as binding that occurred in the presence of 10 μM BTCP. The $K_i$ was determined using standard methods The $IC_{50}$ of DA reuptake inhibition was determined by measuring the degree to which various concentration of beloxepin inhibited incorporation of [$^3$H]-DA into rat striatum synaptosomes (measurements carried out for 15 min at 37° C.).

Results. The $K_i$s and $IC_{50}$s of beloxepin for the NE, 5HT and DA transporters are provided below, showing that beloxepin is a weak, albeit selective, inhibitor of NE reuptake.

$K_i^{NET}$=700 nM
$IC_{50}^{NE}$=130 nM
$K_i^{SERT}$=27% inhibition of binding at 10 μM in a competition assay
$K_i^{DAT}$=16% inhibition of binding at 10 μM in a competition assay Example 3

Beloxepin Inhibition of Cytochrome P450 Isoenzyme CYP2D6

Protocol. The inhibitory activity of beloxepin on cytochrome P450 function was tested using the methods of Chauret (Chauret et al., 2001, Drug Metabolism and Disposition, 29(9), 1196-1200) using 7-methoxy-4-(aminomethyl)-coumarin (MAMC) (Venhorst et al., 2000, European Journal of Pharmaceutical Sciences 12(2): 151-158) as substrate. The source of the enzyme was microsomes containing human recombinant CYP2D6 obtained from BD Bioscience. Conversion of MAMC to 7-hydroxy-4-(aminomethyl)coumarin was measured using a PerkinElmer Fusion with a 390 nm excitation filter and a 460 nm emission filter.

Results. Beloxepin was found to inhibit CYP2D6 activity with an $IC_{50}$=536 nM.

Evaluation of beloxepin as a Direct Inhibitor of Human CYP2D6 (dextromethorphan O-demethylation): Microsomal Incubations for $IC_{50}$ Estimation Protocol: The ability of Beloxepin to inhibit dextromethorphan O-demethylation (CYP2D6) was investigated using pooled male human hepatic microsomes. Beloxepin was incubated with human liver microsomes at concentrations of 0, 0.1, 0.3, 1, 3, 10, 30 and 100 μM Beloxepin. The 200 μL incubations were conducted in duplicate in 0.1 M potassium phosphate buffer (pH 7.4) with 0.02 mg of microsomal protein, 3 mM $MgCl_2$, 1 mM EDTA and 7.5 μM of the probe substrate dextromethorphan in a 96-well polypropylene plate maintained at 37° C. After a 3-minute pre-incubation, the reaction was initiated with the addition of 2 mM NADPH. Upon completion of the 10-minute incubation period, aliquots of 100 μL were removed and added to a new plate containing 100 μL of internal standard in acidified acetonitrile to stop the reaction. The quenched samples were vortexed and the precipitated protein was removed by centrifugation. Supernatant aliquots of 100 μL were transferred to LC vials and 5 μL were injected onto the HPLC system for LC/MS/MS analysis of the metabolite dextrorphan. Standards and quality control samples were similarly prepared using authentic dextrorphan standards.

Analytical Method

Dexthorphan concentrations were determined by high performance liquid chromatography with tandem mass spectrometric detection (LC/MS/MS) after protein precipitation with acidified acetonitrile containing internal standard. Separations were performed with a Flux Rheos 2000 quaternary pump (Leap Technologies, Inc., Carrboro, N.C.) using an XTerra® MS $C_{18}$, 3.5 μm, 4.6×50 mm column (Waters Corporation, Milford, Mass.). Dextrorphan and the internal standard were eluted with 10 mM ammonium formate with 0.1% formic acid: 0.1% formic acid in acetonitrile (80:20, v/v) run under gradient conditions at 1.0 mL/min. A MDS Sciex API4000 (Applied Biosystems, Foster City, Calif.) triple quadrupole mass spectrometer equipped with a Turbo Ionspray ionization source was used as the detector. The instrument was operated in positive ion mode using multiple reaction monitoring (MRM) with specific precursor-product ion pairs for dextrorphan and the internal standard. The mass transitions were m/z 280.2>262.2 for the internal standard and m/z 258.2>157.0 for dextrorphan. Dextrorphan and the internal standard had retention times of approximately 1.54 and 2.00 minutes, respectively.

Results. In this assay (dextromethorphan O-demethylation), Beloxepin was found to inhibit CYP2D6 activity with an $IC_{50}$=31.7 μM (FIG. 15).

Example 4

Beloxepin is Effective in Treating Neuropathic Pain

Preparation of Vehicle and beloxepin formulations. For this Example and all that follow, unless indicated otherwise, beloxepin formulations for injection were prepared using acidified sterile water for injection (SWIJ) as a diluent. To start, a few drops (never more than 400 μl for a final volume of approximately 14 ml) of 1 M HCl was added to neat beloxepin. Glass beads were added and the solution vortexed vigorously for 2-3 minutes, followed by sonication in a water bath for 3-5 minutes to break up larger particles. The SWIJ was then added to QS to final total volume, the formulation vortexed for 2-3 minutes and then sonicated in warm water for approximately 30-60 minutes. Beloxepin was formulated as a 10 mg/ml solution.

For this Example and all that follow, unless indicated otherwise, control vehicle was prepared using the same volumes of 1 M HCl and SWIJ diluent as the test beloxepin formulation.

Protocol. The antiallodynic activity of beloxepin was tested in vivo using the L5-Single Nerve Ligation ("SNL") model of non-nociceptive neuropathic pain as described in LaBuda & Little, 2005, J. Neurosci. Methods 144:175-181. The test animals were placed in a Plexiglas chamber (10 cm×20 cm×25 cm) and habituated for 15 minutes. The chamber was positioned on top of a mesh screen so that von Frey monofilaments could be presented to the plantar surface of both hindpaws. Measurement of tactile sensitivity for each hind paw were obtained using the up/down method (Dixon, 1980, Annu Rev. Pharmacol. Toxicol. 20:441-462) with seven Frey monofilaments (0.4, 1, 2, 4, 6, 8 and 15 grams). Each trial started with a von Frey force of 2 grams delivered to the right hind paw for approximately 1-2 seconds and then the left hind paw. If there was no withdrawal response, the next higher force was delivered. If there was a response, the next lower force was delivered. This procedure was performed until no response was made at the highest force (15 grams) or until four stimuli were administered following the initial response. The 50% paw withdrawal threshold for each paw was calculated using the following formula: [Xth] log=[vFr] log+ky, where [vFr] is the force of the last von Frey used, k=0.2249 which is the average interval (in log units) between the von Frey monofilaments, and y is a value that depends upon the pattern of withdrawal responses (Dixon, 1980, supra). If an animal did not respond to the highest von Frey monofilament (15 grams), then the paw was assigned a value of 18.23 grams. Testing for tactile sensitivity was performed twice and the mean 50% withdrawal value assigned as the tactile sensitivity for the right and left paws for each animal. All test groups contained at least six animals.

Results. The antiallodynic effects produced by beloxepin (30 mg/kg IP) in L5 SNL rats 14 days post surgery are illustrated in FIG. 1. In this experiment, at 14 days post surgery, rats were treated with vehicle or beloxepin (30 mg/kg IP) and tested for tactile allodynia at 30, 60, 120 and 240 min post treatment. Vehicle-treated rats were tested at 30 min post treatment. As illustrated in FIG. 1, beloxepin produced significant antiallodynia effects at the 30, 60 and 120 min time points, with a maximal effect at 30 min post treatment (829% of the threshold of vehicle-treated rats). The magnitude of tactile allodynia observed at the 30 min time point was amongst the highest the inventors have observed in this model. No side effects were observed following treatment.

Example 5

Beloxepin Exerts its Antiallodynic Effect in a Dose-Dependent Fashion

Protocol. A dose response experiment was performed in L5 SNL rats at 16 days post surgery (3, 10 and 30 mg/kg IP beloxepin). In the experiment, animals were tested for tactile allodynia at 30 min post treatment. The sham-operated control group, which were operated on but not subject to nerve ligation, contained 4 animals. The treatment group contained at least six animals.

The results of the dose-response experiment are illustrated in FIG. 2. The 30 mg/kg dose produced a robust antiallodynic effect (852% of the threshold for vehicle-treated rats, and almost equal to that of the sham-operated animals). The results observed replicated the significant antiallodynic effect observed in the time-course experiments of Example 4.

Example 6

Beloxepin is Superior to NE Reuptake Inhibitors, Mixed Serotonin/NE Reuptake Inhibitors and Tricyclic Antidepressants in Treatment of Neuropathic Pain The results of a direct comparison of beloxepin with reboxetine, are illustrated in FIG. 3, and demonstrate that beloxepin is approximately 4-fold more effective. Similarly, FIG. 5 depicts the results of a direct comparison of the antiallodynic effects produced by beloxepin, duloxetine, amitriptyline, and beloxepin in the rat L5 Spinal Nerve Ligation Model (30 mg/kg IP; * p<0.05 compared to vehicle-treated L5 SNL rats; rats were tested at 30 minutes or, for amitriptyline, 60 minutes post-drug administration). The data indicate that beloxepin was the most effective of the compounds tested.

Example 7

Beloxepin Therapy is Effective when Administered Orally

Protocol. A time course experiment was performed with beloxepin (60 mg/kg PO) in L5 SNL rats at 8-days post surgery. Rats were tested at 30, 60, 120 and 240 min post beloxepin. All test groups contained at least six animals.

Results. The results are provided in FIG. 4. Oral beloxepin produced significant and robust antiallodynic effects at the 30 and 60 min time points.

Example 8

Beloxepin is Effective at Treating Acute Nociceptive Pain

Protocol. The ability of beloxepin to treat acute nociceptive pain was demonstrated in the rat hot plate model utilizing Male Sprague-Dawley rats (150-250 g). For the experiment, rats were acclimated to a 50° C. hot plate apparatus by gently placing them on the hot plate with all four paws on the surface. A timer was started and the latency (in seconds) until the rat licked any of its paws was measured. A 60 second cut-off to elicit a response was set to prevent tissue damage to the paws. After the rats elicited the paw lick response, they were removed from the apparatus and returned to their home cages for at least 30 minutes. Baseline paw lick latencies were determined prior to drug treatments in an identical manner to the acclimation test. Following drug treatments, the rats were placed on the hot plate apparatus at the appropriate time and treatment paw lick latencies were determined. All test groups contained at least six animals.

Results. The results of the experiment are illustrated in FIGS. 6A and 6B. FIG. 6A shows the latency (in seconds) between placement on the hot plate and paw lick response. 30 and 60 mg/kg beloxepin (IP) exhibited a statistically significant robust anti-nociceptive effects, with both dosages producing anti-nociceptive activity nearly as effective as 3 mg/kg morphine. FIG. 6B shows the percentage of maximal effect achieved (% MPE) in the same experiment. The paw lick latency was used to determine % MPE for each rat based on the following formula:

$$\% \ MPE = \left[ \frac{\text{Treatment Latency(sec)} - \text{Baseline Latency (sec)}}{60 \text{ sec} - \text{Baseline Latency (sec)}} \right] \times 100$$

Thus, any rats that reach the cut-off have obtained 100% MPE.

Example 9

Beloxepin is Effective at Treating Inflammatory Pain

Protocol. The ability of beloxepin to treat inflammatory pain was tested using Freund's Complete Adjuvant (FCA)- induced mechanical hyperalgesia in rats. For the assay, the methods of DeHaven-Hudkins et al., 1999, J. Pharmacol. Exp. Ther. 289:494-502 were used to determine mechanical hyperalgesia in rats 24 hours after intraplantar administration of 150 μL Freund's Complete Adjuvant (FCA). To determine paw pressure thresholds, the rats were lightly restrained in a gauze wrap and pressure was applied to the dorsal surface of the inflamed and uninflamed paw with a conical piston using a pressure analgesia apparatus (Stoelting Instruments, Wood Dale, Ill.). The paw pressure threshold was defined as the amount of force (in grams) required to elicit an escape response using a cutoff value of 250 grams. Paw pressure thresholds were determined before and at specified times after drug treatment. All test groups contained at least six animals.

Results. The results are illustrated in FIG. 7. 30 mg/kg beloxepin nearly completely reversed hyperalgesia induced by the FCA.

Example 10

Beloxepin is Effective at Treating Visceral Pain

Protocol. The ability of beloxepin to treat visceral pain was demonstrated in a rodent model of acetic acid-induced writhing For the assay, male ICR mice (20-25 g) were treated with vehicle or test compound orally 25 min prior to the intraperitoneal administration of 0.6% of acetic acid. Five minutes after treatment with acetic acid, the number of writhes was counted for 10 min. A writhe is defined as the extension of both front and hind limbs with a concave stretch of the abdomen. The mean number of writhes was determined for each treatment group and the percent inhibition of the vehicle response was calculated using the following formula:

$$1 - \left[ \frac{\text{Number of writhes after treatment}}{\text{Number of writhes in vehicle treated mice}} \right] \times 100$$

All test groups contained at least six animals.

Results. The results are illustrated in FIG. 8. Beloxepin inhibited acetidc acid-induced writhing in a dose-dependent fashion, with an $ED_{50}$ of 13.3 mg/kg (oral).

Example 11

A Mixture of (+)-Beloxepin and (−)-Beloxepin is Effective in an Animal Model of Inflammatory Pain (FCA-Induced Mechanical Hyperalgesia)

Protocol. A sample of (±)-beloxepin was prepared by milling the isolated (+)-beloxepin and (−)-beloxepin enantiomers together, bringing them up in solvent, and then removing the solvent ("Lot 9"). In this experiment, 30 mg/kg of (±)-beloxepin ("Lot 7") or 30 mg/kg of the reconstituted racemic mixture (Lot 9) was administered in rats treated with FCA for 24 hours. Thirty minutes after treatment with vehicle, (±)-beloxepin, or reconstituted racemic mixture, paw pressure thresholds were determined. Thirty minutes is the time of peak mechanical antihyperalgesia of (±)-beloxepin.

Results. As illustrated in FIG. 9, similar mechanical antihyperalgesic (96±16% vs. 77±11%) efficacy was observed in rats treated with (±)-beloxepin or the reconstituted racemic mixture. Thus, a chemical entity that produces significant mechanical antihyperalgesia can be provided as the mixture of its two component enantiomers.

Example 12

Beloxepin is Effective in an Animal Model of Neuropathic Pain (Rat L5 SNL Model)

Protocol. A time course experiment was performed with beloxepin (60 mg/kg PO in L5 SNL rats at 7 days post-surgery. Rats were tested at 30, 60, 120, and 240 minutes post-drug.

Results. Beloxepin produced significant antiallodynic effects at all four time points, as illustrated in FIG. 10.

Protocol. In a further experiment with this animal model of pain, a comparison of the time courses for mechanical antiallodynia in the rat L5 SNL model for beloxepin, duloxetine (a drug approved for the treatment of diabetic neuropathy), and esreboxetine (a compound in Phase III clinical trials for the treatment of fibromyalgia and diabetic neuropathy). The data obtained are depicted in FIG. 11.

Results. As demonstrated in FIG. 11, racemic beloxepin (30 mg/kg IP) was comparable in efficacy to duloxetine (30 mg/kg IP), and the peak antiallodynic effect of racemic beloxepin was greater than that measured in rats treated with esreboxetine (30 mg/kg IP).

Example 13

Beloxepin is Effective in an Animal Model of Post-Operative Pain (Rat Hindpaw Incisional Pain Model)

Protocol. A time course experiment was performed with beloxepin in the hindpaw incision model. At 24 hours post surgery, rats received vehicle or beloxepin (30 mg/kg IP). Rats were tested for tactile allodynia at 30, 60, 120 and 240 minutes after administration of beloxepin.

Results. As illustrated in FIG. 12, racemic beloxepin produced a significant antiallodynic effect at all four time points (maximum hindpaw withdrawal threshold ~29 grams or 544% of the threshold value for vehicle treated rats at the 30 minute time point). The antiallodynic effect produced by racemic beloxepin in this assay is considered very robust.

Protocol. A second time course experiment was performed with racemic beloxepin in the hindpaw incision model after oral (PO) administration. At 24 hours post-surgery, rats received vehicle or racemic beloxepin (60 mg/kg PO). Rats were tested for tactile allodynia at 30, 60, 120 and 240 minutes after administration of beloxepin.

Results. As illustrated in FIG. 13, racemic beloxepin produced a significant antiallodynic effect at all four time points (maximum hindpaw withdrawal threshold ~24 grams at the 30 and 60 minute time points). The antiallodynic effect produced by beloxepin in this assay is considered very robust and is comparable to the effect that was observed after IP administration.

Protocol. A third time course experiment was performed with racemic beloxepin in the hindpaw incision model after intravenous (IV) administration. At 24 hours post-surgery, rats received vehicle or beloxepin (3 mg/kg IV). The 3 mg/kg IV dose is a dose that is 10-fold lower than a dose that produced a significant respiratory or cardiovascular side effect. Rats were tested for tactile allodynia at 30, 60, 120 and 240 minutes after administration of beloxepin.

Results. As illustrated in FIG. 14, racemic beloxepin produced a significant antiallodynic effect at the 30 and 120 minute time points (maximum hindpaw withdrawal threshold ~21 grams at the 30 minute time point). The antiallodynic effect produced by beloxepin in this assay at the 30 minute time point is considered very robust and comparable to the antiallodynic effect observed with a dose of 60 mg/kg PO of racemic beloxepin at the 30 minute time point.

While various specific embodiments have been illustrated and described, it will be appreciated that various changes can be made without departing from the spirit and scope of the invention(s).

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. A method of treating pain in a mammal, comprising administering to a mammal suffering from pain an amount of beloxepin, or a salt thereof, effective to treat the pain.

2. The method of claim 1 in which the mammal is a human.

3. The method of claim 1 in which the beloxepin is administered parenterally.

4. The method of claim 1 in which the beloxepin is administered orally.

5. The method of claim 1 in which the pain is acute pain of nociceptive origin.

6. The method of claim 5 in which the pain is cancer pain.

7. The method of claim 5 in which the pain is surgical pain.

8. The method of claim 1 in which the pain is chronic pain of nociceptive origin.

9. The method of claim 8 in which the pain is inflammatory pain.

10. The method of claim 8 in which the pain is cancer pain.

11. The method of claim 1 in which the pain is chronic pain of non-nociceptive origin.

12. The method of claim 11 in which the pain is neuropathic pain.

13. The method of claim 1 in which the pain is inflammatory pain.

14. The method of claim 1 in which the pain is visceral pain.

15. The method of claim 1 in which the beloxepin, or a salt thereof, is administered to the mammal in the form of a composition.

16. The method of claim 15 in which the beloxepin is included in the composition as a salt.

17. The method of claim 15 in which the beloxepin is included in the composition as a free base.

18. The method of claim 15 in which the composition is formulated for oral administration.

* * * * *